US008841099B2

(12) United States Patent
Boddy et al.

(10) Patent No.: US 8,841,099 B2
(45) Date of Patent: Sep. 23, 2014

(54) CELL-BASED PRODUCTION OF NONULOSONATES

(75) Inventors: Christopher N. Boddy, Ottawa (CA); Susan M. Logan, Ottawa (CA); Benjamin R. Lundgren, Nampa, ID (US); Ian C. Schoenhofen, Stittsville (CA); Dennis M. Whitfield, Ottawa (CA)

(73) Assignees: National Research Council of Canada, Ottawa, ON (CA); University of Ottawa, Ottawa, ON (CA)

( * ) Notice: Subject to any disclaimer, the term of this patent is extended or adjusted under 35 U.S.C. 154(b) by 0 days.

(21) Appl. No.: 13/642,308

(22) PCT Filed: Apr. 20, 2011

(86) PCT No.: PCT/CA2011/000449
§ 371 (c)(1),
(2), (4) Date: Oct. 19, 2012

(87) PCT Pub. No.: WO2011/130836
PCT Pub. Date: Oct. 27, 2011

(65) Prior Publication Data
US 2013/0196381 A1    Aug. 1, 2013

Related U.S. Application Data

(60) Provisional application No. 61/326,015, filed on Apr. 20, 2010.

(51) Int. Cl.
| | |
|---|---|
| *C12P 7/40* | (2006.01) |
| *C12P 7/42* | (2006.01) |
| *C12P 1/02* | (2006.01) |
| *C12N 1/14* | (2006.01) |
| *A61K 38/00* | (2006.01) |
| *C12N 15/52* | (2006.01) |
| *C12N 15/70* | (2006.01) |
| *C12P 19/30* | (2006.01) |
| *C12P 19/26* | (2006.01) |

(52) U.S. Cl.
CPC ............. *C12N 15/70* (2013.01); *C12N 15/52* (2013.01); *C12P 19/305* (2013.01); *C12P 19/26* (2013.01)
USPC .......................... 435/146; 435/69.1; 435/170

(58) Field of Classification Search
None
See application file for complete search history.

(56) References Cited

FOREIGN PATENT DOCUMENTS

| WO | 2008097366 | 8/2008 |
| WO | 2008097366 A2 | 8/2008 |

OTHER PUBLICATIONS

Chiba, Y., and Jigami, Y., 2007, Curr. Opin. Chem. Biol., 11: 670-676.
Colombo, J. P.; Garcia-Rodenas, C.; Guesry, P. R.; Rey, J. Acta. Paediatr. Suppl. 2003, 92, 42-46.
Erbel, P. J. A.; Barr, K.; Gao, N.; Gerwig, G. J.; Rick, P. D.; Gardner, K. H. J. Bacteriol. 2003, 185, 1995-2004.
Glaze, P. A.; Watson, D. C.; Young, N. M.; Tanner, M. E. Biochemistry 2008, 47, 3272-3282.
Higgins, E., 2010, Glycoconj. J., 27: 211-225WO 2008/097366.
Hofmann, M.; Boles, E.; Zimmerman, F. K. Eur. J. Biochem. 1994, 221, 741-747.
Hsu, T. L.; Hanson, S. R.; Kishikawa, K.; Wang, S. K.; Sawa, M.; Wong, C. H. Proc. Natl. Acad. Sci. U.S.A. 2007, 104, 2614-2619.
Itoh, Y.; Rice, J. D.; Goller, C.; Pannuri, A.; Taylor, J.; Meisner, J.; Beveridge, T. J.; Preston, J. F.; Romeo, T. J. Bacteriol. 2008, 190, 3670-3680.
Jayant, S.; Khandare J. J.; Wang, Y.; Singh, A. P.; Vorsa, N.; Minko, T. Pharm. Res. 2007, 24, 2120-2130.
Kang et al. (2004) Systemic Mutagenesis of the *Escherichia coli* Genome. Journal of Bacteriology. 186. pp. 4921-4930.
Keseler, I. M.; Bonavides-Martinez, C.; Collado-Vides, J.; Gama-Castro, S.; Gunsalus, R. P. ; Johnson, D. A.; Krummenacker, M.; Nolan, L. M.; Paley, S.; Paulsen, I. T.; Peralta-Gil, M.; Santos-Zavaleta, A.; Shearer, A. G.; Karp, P. D. Nucleic Acid Res. 2009, 37, D464-D470.
Kiss, E.; Kereszt, A.; Barta, F.; Stephens, S.; Reuhs, B. L.; Kondorosi, A.; Putnoky, P. Mol. Plant Microbe Interact. 2001, 14, 1395-1403.
Knirel, Y. A.; Shashkov, A. S.; Tsvetkov, Y. E.; Jansson, P. E.; Zahringer, U. Adv. Carbohydr. Chem. Biochem. 2003, 58, 371-417.
Lee, Y.J.; , Kubota, A.; Ishiwata, A.; Ito, Y. Tetrahedron Lett. 2010, 52, 418.
Lewis, A. L.; Desa, N.; Hansen, E. E.; Knirel, Y. A.; Gordon, J. I.; Gagneux, P.; Nizet, V.; Varki, A. Proc. Natl. Acad. Sci. U.S.A. 2009, 106, 13552-13557.
Lin et al., 2006, Appl. Microbiol. Biotechnol., 71: 870-874.
Linton, D.; Dorrell, N.; Hitchen, P. G.; Amber, S.; Karlyshev, A. V.; Morris, H. R.; Dell, A.; Valvano, M. A.; Aebi, M.; Wren, B. W. Mol. Microbiol. 2005, 55, 1695-1703.
Lundgren B .R.and Christopher N. Boddy Sialic acid and N-acyl sialic acid analog production by fermentation of metabolically and genetically engineered *Escherichia coli* Org. Biomol. Chem., 2007, 5, 1903-1909.
Lundgren, B.R. (2010). Metabolically and genetically engineering *Escherichia coli* for the production of sialic acid and sialic acid analogs. Doctoral dissertation, Syracuse University, Syracuse, New York, USA.
Mahal, L. K.; Yarema K. J.; Bertozzi, C. R. Science 1997, 276, 11251128.
Manzi, A. E.; Diaz, S.; Varki, A. Anal. Biochem. 1990, 188, 20-32.

(Continued)

*Primary Examiner* — Suzanne M Noakes
*Assistant Examiner* — Gerard Lacourciere
(74) *Attorney, Agent, or Firm* — Dahna S. Pasternak; Pasternak Patent Law

(57) ABSTRACT

The present invention relates to the cell-based production of bacterial nonulosonates and their biosynthetic precursors. Specifically, the present invention provides recombinant cells for the production of pseudaminic acid, legionaminic acid, UDP-2,4-diacetamido-2,4,6-trideoxy-β-L-altropyranose, and UDP-2,4-diacetamido-2,4,6-trideoxy-α-D-glucopyranose. Methods for producing the sugars are also provided.

11 Claims, 10 Drawing Sheets

(56) References Cited

OTHER PUBLICATIONS

McNally, D. J.; Aubry, A. J.; Hui, J. P. M.; Khieu, N. H.; Whitfield, D.; Ewing, C. P.; Guerry, P.; Brisson, J. R.; Logan, S. M.; Soo, E. C. J. Biol. Chem. 2007, 282, 14463-14475.

Mio, T.; Yabe, T.; Arisawa, M.; Yamada-Okabe, H. J. Biol. Chem. 1998, 273, 14392-14397.

Oliver, N. B.; Chen, M. M.; Behr, J. R.; Imperiali, B. Biochemistry 2006, 45, 13659-13669.

Plumbridge, J. A.; Cochet, O.; Souza, J. M.; Altamirano, M. M.; Calcagno, M. L.; Badet, B. J. Bacteriol. 1993, 175, 4951-4956.

Plumbridge, J.; Vimr, E. J. Bacteriol. 1999, 181, 47-54.

Rice J.D., Carlos Goller, Archana Pannuri, Jeannette Taylor, Jeffrey Meisner, Terry J. Beveridge, James F. Preston III, and Tony Romeo (2008), Roles of pgaABCD Genes in Synthesis, Modification, and Export of the *Escherichia coli* Biofilm Adhesin Poly-β-1,6-N-Acetyl-D-Glucosamine Journal of Bacteriology,190, 3670-3680.

Schoenhofen, I. C.; McNally, D. J.; Brisson, J.; Logan, S. M. Glycobiology 2006a, 16, 8C-14C.

Schoenhofen, I. C.; McNally, D. J.; Vinogradov, E.; Whitfield, D.; Young, N. M.; Dick, S.; Wakarchuk, W. W.; Brisson, J.; Logan, S. M. J. Biol. Chem. 2006b, 281, 723-732.

Schoenhofen, I. C.; Vinogradov, E.; Whitfield, D.; Brisson, J.; Logan, S. M. Glycobiology 2009, 19, 715-725.

Sethuraman, N., and Stadheim, T.A. 2006, Curr. Opin. Biotechnol., 17: 341-346.

Studier, F. W.; Rosenberg, A. H.; Dunn, J. J.; Dubendorff, J. W. Methods Enzymol. 1990, 185, 60-89.

Tsvetkov, Y.E., Shashkov, A.S., Knirel, Y.A., and Zahringer, U., 2001, Carbohydrate Research, 335:221-243.

von Itzstein, M. Nat. Rev. Drug Discovery 2007, 6, 967-974.

Wang, B.; Yu, B.; Karim, M.; Hu, H.; Sun, Y.; McGreevy, P.; Petocz, P.; Held, S.; Brand-Miller, J. Am. J. Clin. Nutr. 2007, 85, 561-569.

PCT ISR for PCT/CA2011/000449.

PCT Written Opinion for PCT/CA2011/000449.

| gene cluster | # of genes | sugar unit |
|---|---|---|
| ECA | 12 | $\left[3\text{FucN4Ac}\alpha1 - 4\text{ManNAcA}\beta1 - 4\text{GlcNAc}\alpha1\right]_n$ |
| colanic acid | 20 | $\begin{array}{c} \phantom{xxxxxxxxxxxxxx} 6\\ \phantom{xxxxxxxxxxxxx} \text{or}\;_3\text{Pyr}\\ \phantom{xxx} 1\beta\text{Gal}3 - 1\beta\text{GlcA}4 - 1\beta\text{Gal}\;^3_4\,\text{Pyr}\\ \left[3\text{Fuc}\alpha1 - 4\text{Fuc}\beta1 - 3\text{Glc}\beta1\right]_n\\ \phantom{xxxxxxxxx}|\\ \phantom{xxxxxxx}\text{OAc} \end{array}$ |
| poly-$N$-acetyl-glucosamine | 4 | $\left[6\text{GlcNAc}\beta1 - 6\text{GlcNAc}\beta1\right]_n$ |

FIG. 3

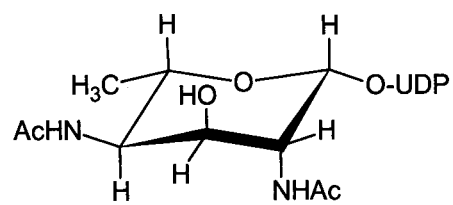
UDP-2,4-diacetamido-2,4,6-trideoxy-β-L-altropyranose
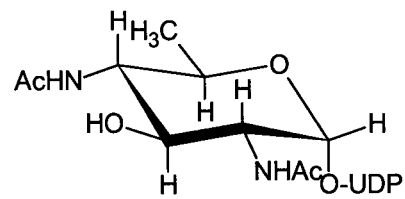
UDP-2,4-diacetamido-2,4,6-trideoxy-α-D-glucopyranose
FIG. 11

CELL-BASED PRODUCTION OF NONULOSONATES

This application is a national entry of International Patent Application PCT/CA2011/000449 filed Apr. 20, 2011 and claims the benefit of U.S. Provisional Patent Application U.S. Ser. No. 61/326,015 filed Apr. 20, 2010, the entire contents of both of which are hereby incorporated by reference.

FIELD OF THE INVENTION

The present invention relates to the cell-based production of bacterial nonulosonates. More specifically, the present invention relates to the cell-based production of bacterial nonulosonates and their biosynthetic precursors.

BACKGROUND OF THE INVENTION

Nonulosonic sugars are a family of nine-carbon α-keto acids that are predominantly found on the outer surfaces of both eukaryotic and bacterial cells. Sialic acid (see FIG. 1), which is the best characterized member of this family, plays a crucial role in animal physiology; for this reason, sialic acid and its derivatives have been extensively used as drug targeting molecules (Javant et al, 2007), anti-viral drugs (von Itzstein, 2007), cell-imaging agents (Mahal et al, 1997; Hsu et al, 2007), and as supplements in nutraceuticals (Colombo et al, 2003; Wang et al, 2007).

Two other structurally distinct nonulosonic sugars, pseudaminic (Schoenhofen et al, 2006a) (Pse) and legionaminic (Schoenhofen et al, 2009) (Leg) acid (FIG. 1), and their biosynthetic pathways have also been characterized. These sialic acid-like sugars are constituents of microbial glycans, which are associated with important virulence factors, including flagella (McNally et al, 2007), capsules (Kiss et al, 2001), and lipopolysacchrides (Knirel et al, 2003 (LPS). Many commensal, as well as pathogenic bacteria, notably *Campylobacter jejuni*, *Campylobacter coli*, *Clostridium botulinum*, *Escherichia coli* O161, *Helicobacter pylori*, *Legionella pneumophila*, *Vibrio parahaemolyticus* and *Pseudomonas aeruginosa*, biosynthesize and decorate their surfaces with these nonulosonic acids, whose function(s) remains unclear.

The structural similarities and evolutionary history (Lewis et al, 2009) shared between these three nonulosonic sugars has raised considerable interest in understanding the mammalian sialobiology associated with bacterial-derived Pse and Leg. The biosynthesis of Pse and Leg parallels that of sialic acid and involves the condensation of a 6-carbon amino sugar intermediate with phosphoenolpyruvate (PEP) to generate the corresponding nonulosonate. In contrast to sialic acid biosynthesis in bacteria, which involves condensation of N-acetylmannosamine (ManNAc) with PEP, both Pse and Leg utilize unusual 2,4-diacetamido-2,4,6-trideoxy hexoses (DATDH) for the synthase step.

Pse is biosynthesized from UDP-N-acetylglucosamine (UDP-GlcNAc) in a five-step enzymatic transformation (Schoenhofen et al, 2006a) (see Table 1 and FIG. 2). A dedicated dehydratase (PseB) and aminotransferase (PseC) pair (Schoenhofen et al, 2006b), converts UDP-GlcNAc into UDP-4-amino-4,6-dideoxy-β-L-AltNAc. An acetyltransferase, PseH, and a UDP-sugar hydrolase, PseG, transform this UDP-activated sugar intermediate into 2,4-diacetamido-2,4,6-trideoxy-L-altropyranose (6-deoxy-AltdiNAc). The Pse synthase, PseI, performs the PEP-dependent condensation with 6-deoxy-AltdiNAc to liberate 5,7-diacetamido-3,5,7,9-tetradeoxy-L-glycero-L-manno-nonulosonic acid or pseudaminic acid.

TABLE 1

The enzymes involved in UDP-6-deoxy-AltdiNAc, pseudaminic acid (Pse), UDP-BacdiNAc and legionaminic acid (Leg) biosynthesis. Enzymes are shown in sequential order, where each product is a substrate for the next biosynthetic step. The initial substrate for each pathway is UDP-GlcNAc.

| Enzyme Nomenclature | In vitro Enzyme function | Biosynthetic product(s) |
|---|---|---|
| *UDP-6-deoxy-AltdiNAc and Pseudaminic acid route* | | |
| PseB | UDP-GlcNAc 4,6-dehydratase and 5-epimerase | UDP-2-acetamido-2,6-dideoxy-β-L-arabino-hexos-4-ulose |
| PseC | aminotransferase | UDP-4-amino-4,6-dideoxy-β-L-AltNAc or UDP-2-acetamido-4-amino-2,4,6-trideoxy-β-L-Alt |
| PseH | N-acetyltransferase | UDP-2,4-diacetamido-2,4,6-trideoxy-β-L-Alt (UDP-6-deoxy-AltdiNAc) |
| PseG | UDP-sugar hydrolase | 2,4-diacetamido-2,4,6-trideoxy-L-Alt (6-deoxy-AltdiNAc) |
| PseI | Pse synthase | 5,7-diacetamido-3,5,7,9-tetradeoxy-L-glycero-L-manno-nonulosonic acid (Pse) |
| *UDP-BacdiNAc and Legionaminic acid route* | | |
| PglF | UDP-GlcNAc 4,6-dehydratase | UDP-2-acetamido-2,6-dideoxy-α-D-xylo-hexos-4-ulose |
| PglE | aminotransferase | UDP-4-amino-4,6-dideoxy-α-D-GlcNAc or UDP-2-acetamido-4-amino-2,4,6-trideoxy-α-D-Glc |
| PglD | N-acetyltransferase | UDP-2,4-diacetamido-2,4,6-trideoxy-α-D-Glc (UDP-BacdiNAc) |
| LegG | UDP-sugar hydrolase and 2-epimerase | 2,4-diacetamido-2,4,6-trideoxy-D-Man (6-deoxy-MandiNAc) |
| LegI | Leg synthase | 5,7-diacetamido-3,5,7,9-tetradeoxy-D-glycero-D-galacto-nonulosonic acid (Leg) |

Leg may also be biosynthesized from UDP-N-acetylglucosamine (UDP-GlcNAc) in a five-step enzymatic transformation (Schoenhofen et al, 2009; Schoenhofen et al, 2006b; Oliver et al, 2006; Glaze et al, 2008; see Table 1 and FIG. 2). Dehydratase PglF and aminotransferase PglE pair (Schoenhofen et al, 2006b) convert UDP-GlcNAc into UDP-4-amino-4,6-dideoxy-α-D-GlcNAc. Acetyltransferase PglD and hydrolyzing 2-epimerase LegG transform this UDP-activated sugar intermediate into 2,4-diacetamido-2,4,6-trideoxy-D-mannopyranose (6-deoxy-MandiNAc). The Leg synthase, LegI, performs the PEP-dependent condensation with 6-deoxy-MandiNAc to liberate 5,7-diacetamido-3,5,7,9-tetradeoxy-D-glycero-D-galacto-nonulosonic acid (legionaminic acid). Enzymes functionally similar to PglF, PglE and PglD also exist, for example the *C. jejuni* LegB, LegC and LegH (respectively) enzymes, which produce identical sugar products except that they are GDP-linked biosynthetic intermediates (Schoenhofen et al, 2009). Here, PglFED produce UDP-BacdiNAc starting from UDP-GlcNAc (see Table 1). Similarly, certain LegG enzymes, as in *C. jejuni*, may utilize a GDP-linked substrate The bacterial nonulosonic acids are a medically and biotechnologically important family of cell-surface carbohydrates. Current methods for producing these complex sugars allows the isolation of only limited, sub-gram quantities from natural resources, or via currently available chemical or enzymatic synthesis in vitro. Additionally, the cost of enzyme preparation, reagents and cofactors required for in vitro synthesis is quite significant.

There remains a need in the art for a method that can generate significant quantities of Pse and Leg in a cost-effective manner.

SUMMARY OF THE INVENTION

The present invention relates to the cell-based production of bacterial nonulosonates. More specifically, the present invention relates to the cell-based production of bacterial nonulosonates and their biosynthetic precursors.

The present invention provides a recombinant cell for the production of pseudaminic acid, comprising an inactivated GlcNAc-6-P deacetylase gene, a gene encoding PseB enzyme function, a gene encoding PseC enzyme function, a gene encoding PseH enzyme function, a gene encoding PseI enzyme function, a gene encoding PseG enzyme function, a gene encoding a GlcNAc-6-P mutase, and a gene encoding a GlcNAc-1-P uridyltransferase.

In the recombinant cell just described, the PseB, PseC, PseH, and PseI enzyme functions may be genes from *H. pylori*, the PseG enzyme function may be a gene from *C. jejuni*, and the GlcNAc-6-P mutase and GlcNAc-1-P uridyltransferase genes may be from *S. cerevisiae*. Optionally, the recombinant cell may further comprise an inactivated sialic acid transporter gene, an inactivated sialic acid aldolase gene, or a combination thereof; the sialic acid transporter gene may be nanT, and the sialic acid aldolase gene may be nanA.

In the recombinant cell described above, the cell may be an *E. coli* cell.

In one example, in the recombinant cell for the production of pseudaminic acid, the recombinant cell may be an *E. coli* cell, the sialic acid transporter gene may be nanT, the sialic acid aldolase gene may be nanA, the GlcNAc-6-P deacetylase gene may be nagA, the PseB gene may encode SEQ ID NO:1, the PseC gene may encode SEQ ID NO:2, the PseH gene may encode SEQ ID NO:3, the PseI gene may encode SEQ ID NO:4, the PseG gene may encode SEQ ID NO:5, the gene encoding GlcNAc-6-P mutase may be agm1, and the gene encoding GlcNAc-1-P uridyltransferase may be uap1.

In the recombinant cell described above, the growth medium for the recombinant cell may be supplemented with palmitate; alternatively, the recombinant cell may further comprising a gene encoding acetyl-CoA synthase.

One specific example of the recombinant cell for the production of pseudaminic acid as described above is that of IDAC deposit No. 060411-02.

The present invention also provides a recombinant cell for the production of legionaminic acid, comprising an inactivated GlcNAc-6-P deacetylase gene, a gene encoding PglF enzyme function, a gene encoding PglE enzyme function, a gene encoding PglD enzyme function, a gene encoding LegI enzyme function, a gene encoding LegG enzyme function, a gene encoding a GlcNAc-6-P mutase, and a gene encoding a GlcNAc-1-P uridyltransferase.

In the recombinant cell just described, the PglF, PglE, and PglD enzyme functions may be genes from *C. jejuni*, the LegI enzyme function may be genes from *C. jejuni* or *L. pneumophila*, the LegG enzyme function may be a gene from *L. pneumophila* LegG, and the GlcNAc-6-P mutase and GlcNAc-1-P uridyltransferase genes may be from *S. cerevisiae*. Optionally, the recombinant cell may further comprise an inactivated sialic acid transporter gene, an inactivated sialic acid aldolase gene, or a combination thereof; the sialic acid transporter gene may be nanT, and the sialic acid aldolase gene may be nanA. In the recombinant cell described above, the cell may be an *E. coli* cell.

In one example, in the recombinant cell for the production of legionaminic acid, the recombinant cell may be an *E. coli* cell, the sialic acid transporter gene may be nanT, the sialic acid aldolase gene may be nanA, the GlcNAc-6-P deacetylase gene may be nagA, the PglF gene may encode SEQ ID NO:6, the PglE gene may encode SEQ ID NO:7, the PglD gene may encode SEQ ID NO:8, the LegI gene may encode SEQ ID NO:9 or SEQ ID NO:10, the LegG gene may encode SEQ ID NO:11, the GlcNAc-6-P mutase gene may be agm1, and the GlcNAc-1-P uridyltransferase gene may be uap1.

The recombinant cell for the production of legionaminic acid as described above may further comprise an inactivated ManNAc-6-P epimerase gene, an inactivated undecaprenyl-P/UDP-GlcNAc transferase gene, or a combination thereof. The ManNAc-6-P epimerase gene may be nanE, and the undecaprenyl-P/UDP-GlcNAc transferase gene may be wecA.

Additionally, in the recombinant cell for the production of legionaminic acid described above, the growth medium for the recombinant cell may be supplemented with palmitate; alternatively, the recombinant cell may further comprising a gene encoding acetyl-CoA The present invention provides a method for the production of pseudaminic acid (5,7-diacetamido-3,5,7,9-tetradeoxy-L-glycero-L-manno-nonulosonic acid), comprising growing the recombinant cell for the production of pseudaminic acid as described above and recovering the produced pseudaminic acid.

Similarly, the present invention provides a method for the production of legionaminic acid (5,7-diacetamido-3,5,7,9-tetradeoxy-D-glycero-D-galacto-nonulosonic acid), comprising growing the recombinant cell for the production of legionaminic acid as described above and recovering the produced legionaminic acid.

The present invention further provides a recombinant cell for the production of UDP-2,4-diacetamido-2,4,6-trideoxy-β-L-altropyranose (UDP-6-deoxy-AltdiNAc), comprising an inactivated GlcNAc-6-P deacetylase gene, a gene encoding PseB enzyme function, a gene encoding PseC enzyme function, a gene encoding PseH enzyme function, a gene encoding GlcNAc-6-P mutase, and a gene encoding a GlcNAc-1-P uridyltransferase.

In the recombinant cell as just described, the PseB, PseC, and PseH enzyme functions may be from *H. pylori*, and the GlcNAc-6-P mutase and GlcNAc-1-P uridyltransferase genes may be from *S. cerevisiae*. Optionally, the recombinant cell may further comprise an inactivated sialic acid transporter gene, an inactivated sialic acid aldolase gene, or a combination thereof; the sialic acid transporter gene may be nanT, and the sialic acid aldolase gene may be nanA. The recombinant cell as described above may be an *E. coli* cell.

In one example of a recombinant cell for the production of UDP-6-deoxy-AltdiNAc, the recombinant cell may be an *E. coli* cell, the sialic acid transporter gene may be nanT, the sialic acid aldolase gene may be nanA, the GlcNAc-6-P deacetylase gene may be nagA, the PseB gene may encode SEQ ID NO:1, the PseC gene may encode SEQ ID NO:2, the PseH gene may encode SEQ ID NO:3, the GlcNAc-6-P mutase gene may be agm1, and the GlcNAc-1-P uridyltransferase gene may be uap1.

The present invention also provides a method for the production of UDP-2,4-diacetamido-2,4,6-trideoxy-β-L-altropyranose (UDP-6-deoxy-AltdiNAc), comprising growing the recombinant cell for the production of UDP-6-deoxy-AltdiNAc as described above and recovering the produced UDP-2,4-diacetamido-2,4,6-trideoxy-β-L-altropyranose.

The present invention additionally provides a recombinant cell for the production of UDP-2,4-diacetamido-2,4,6-trideoxy-α-D-glucopyranose (UDP-BacdiNAc), comprising an inactivated GlcNAc-6-P deacetylase gene, a gene encoding PglF enzyme function, a gene encoding PglE enzyme function, and a gene encoding PglD enzyme function, a gene encoding GlcNAc-6-P mutase, and a gene encoding a GlcNAc-1-P uridyltransferase.

In the recombinant cell as just described, the PglF, PglE, and PglD genes may be from *C. jejuni*, and the GlcNAc-6-P mutase and GlcNAc-1-P uridyltransferase genes may be from *S. cerevisiae*. Optionally, the recombinant cell may further comprise an inactivated sialic acid transporter gene, an inactivated sialic acid aldolase gene, or a combination thereof; the sialic acid transporter gene may be nanT, and the sialic acid aldolase gene may be nanA.

The recombinant cell for production of UDP-BacdiNAc described above may further comprising an inactivated undecaprenyl-P/UDP-GlcNAc transferase gene. The undecaprenyl-P/UDP-GlcNAc transferase gene may be wecA.

The recombinant cell for production of UDP-BacdiNAc described above may be an *E. coli* cell.

In one example of a recombinant cell for production of UDP-BacdiNAc, the recombinant cell may be an *E. coli* cell, the sialic acid transporter gene may be nanT, the sialic acid aldolase gene may be nanA, the GlcNAc-6-P deacetylase gene may be nagA, the PglF gene may encode SEQ ID NO:6, the PglE gene may encode SEQ ID NO:7, the PglD gene may encode SEQ ID NO:8, the GlcNAc-6-P mutase gene may be agm1, and the GlcNAc-1-P uridyltransferase gene may be uap1.

One specific example of the recombinant cell for the production of UDP-BacdiNAc as described above is that of IDAC deposit No. 060411-01.

The present invention also provides a method for the production of UDP-2,4-diacetamido-2,4,6-trideoxy-α-D-glucopyranose (UDP-BacdiNAc), comprising growing the recombinant cell for the production of UDP-BacdiNAc as described above and recovering the produced UDP-2,4-diacetamido-2,4,6-trideoxy-α-D-glucopyranose.

Additional aspects and advantages of the present invention will be apparent in view of the following description. The detailed description and examples, while indicating preferred embodiments of the invention, are given by way of illustration only, as various changes and modifications within the scope of the invention will become apparent to those skilled in the art in light of the teachings of this invention.

BRIEF DESCRIPTION OF THE DRAWINGS

These and other features of the invention will now be described by way of example, with reference to the appended drawings, wherein:

FIG. 3 shows xopolysaccharides that were deleted in *E. coli* K-12 for the production of pseudaminic acid, including i) enterobacterial common antigen (EGA), ii) colanic acid and iii) poly-N-acetylglucosamine. The 4-acetamido-6-deoxy sugar, fucosamine, is a constituent of EGA and colanic acid. Each gene cluster was removed using lambda Red-mediated recombination. Abbreviations, FucN4Ac: 4-acetamido-4,6-dideoxy-D-galactose, ManNAcA: Nacetyl-D-mannosaminuronic acid, Gal: galactose, Pyr: pyruvate.

FIG. 6A) (PseBCH) and UDP-BacdiNAc (UDP-2,4-diacetamido-2,4,6-trideoxy-α-D-glucopyranose.

FIG. 7A showed a clear ion-extraction peak for Pseudaminic acid with m/z values of 317 (M−OH), 335 (M+H) and 357 (M+Na). These ion extraction peaks were not present in the negative control production culture (data not shown). To confirm that these m/z values are derived from authentic Pseudaminic acid, cell-free broth from the negative control culture was spiked with Pseudaminic acid standard. As shown, the ion-extraction peak of the spiked sample (FIG. 7B) was identical to the Pseudaminic acid produced from the BRL04/pseBCHGI/agm1/uap1 (BRL04/pBRL175/pBRL178) fermentation (FIG. 7A).

FIG. 11 shows the structure of UDP-2,4-diacetamido-2,4,6-trideoxy-β-L-altropyranose (UDP-6-deoxy-AltdiNAc) and UDP-2,4-diacetamido-2,4,6-trideoxy-α-D-glucopyranose (UDO-BacdiNAc), precursors for production of pseudaminic acid and legionamic acid, respectively.

DETAILED DESCRIPTION OF THE INVENTION

Figure 1:
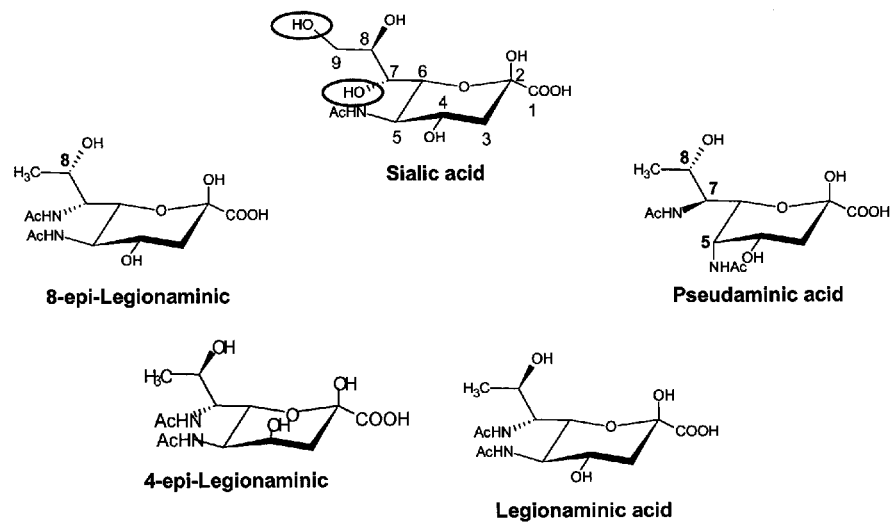
FIG. 1 shows the structures of sialic acid and sialic acid-like sugars. Sialic acid (Neu5Ac; D-glycero-D-galacto configuration), pseudaminic acid (Pse5Ac7Ac; L-glycero-L-manno configuration), legionaminic acid (Leg5Ac7Ac; D-glycero-D-galacto configuration), 4-epi-legionaminic acid (4eLeg5Ac7Ac; D-glycero-D-talo configuration), and 8-epi-legionaminic acid (8eLeg5Ac7Ac; L-glycero-D-galacto configuration) are shown. For reference, the 9 carbon atoms of sialic acid are numbered, and the functional groups that are different than those present on sialic acid-like sugars are circled. Moreover, stereochemical differences of bacterial sialic acid-like sugars to that of sialic acid are indicated by numbering of the respective carbon centers.

The present invention relates to the cell-based production of bacterial nonulosonates. More specifically, the present invention relates to the cell-based production of bacterial nonulosonates and their biosynthetic precursors.

The present invention provides a recombinant cell for the production of pseudaminic acid, comprising an inactivated sialic acid transporter gene, an inactivated sialic acid aldolase gene, an inactivated GlcNAc-6-P deacetylase gene, a gene encoding PseB enzyme function, a gene encoding PseC enzyme function, a gene encoding PseH enzyme function, a gene encoding PseI enzyme function, a gene encoding PseG enzyme function, a gene encoding a GlcNAc-6-P mutase, and a gene encoding a GlcNAc-1-P uridyltransferase.

The present invention also provides a recombinant cell for the production of legionaminic acid, comprising an inactivated sialic acid transporter gene, an inactivated sialic acid aldolase gene, an inactivated GlcNAc-6-P deacetylase gene, a gene encoding PglF enzyme function, a gene encoding PglE enzyme function, a gene encoding PglD enzyme function, a gene encoding LegI enzyme function, a gene encoding LegG enzyme function, a gene encoding a GlcNAc-6-P mutase, and a gene encoding a GlcNAc-1-P uridyltransferase.

By the term "recombinant cell", also referred to herein as "recombinant strain", it is meant any suitable recombinant cell engineered to comprise the appropriate enzymes as listed above. As will be appreciated by one of skill in the art, this may be done using standard molecular biology techniques that are well-known in the art. The recombinant cell may be any suitable microorganism, such as a prokaryotic or eukaryotic cell. For example, the recombinant cell may be a bacterial or yeast cell; the recombinant bacterial or yeast cell may also be a bacterial or yeast strain that has UDP-GlcNAc-utilizing pathways but that does not normally produce the above-listed end products. Alternatively, the recombinant cell may be part of any suitable recombinant expression system, such as mammalian cell lines or insect cell lines (Higgins, 2010; Sethuraman & Stadheim, 2006; Chiba & Jigami, 2007). Without wishing to be limiting in any manner, the recombinant cell may be selected from the group consisting of *Escherichia coli*, *Saccharomyces cerevisiae*, *Pichia pastoris*, *Hansenula polymorpha*, *Kluyveromyces lactis*, *Candida albicans*, Chinese hamster ovary (CHO) cell lines, or murine myeloma cell lines. The recombinant cell does not include naturally-occurring cells that produce pseudaminic or legionamic acid (such as *Escherichia coli* O161), but does include naturally-occurring cells in which the production of pseudaminic or legionamic acid has been increased, improved, or enhanced by engineering to comprise the enzymes listed herein. In a specific, non-limiting example, the recombinant cell may be an *Escherichia coli* cell.

The recombinant cells described herein may be part of a cell-based system for producing the legionaminic acid, pseudaminic acid, or respective biosynthetic precursors. By the term "cell-based system", it is meant that the recombinant strains described herein are one component and others may be included. Components of the system may include, but are not limited to the recombinant cells described herein, culture medium (also referred to herein as "growth medium"), and supplements. The culture medium may be any suitable culture medium; as would be known to those skilled in the biochemical arts, the choice of culture medium may be based on the type of recombinant cell. Without wishing to be limiting in any manner, supplements to the culture medium may include palmitate. In an alternative to supplementation with palmitate, the recombinant cell may further comprise over-expression of a gene encoding acetyl-CoA synthetase, where the enzyme joins acetate and coenzymeA (CoA) to form acetyl-CoA (Lin et al., 2006).

Pseudaminic acid, also referred to herein as "Pse", "Pse5Ac7Ac", or "5,7-diacetamido-3,5,7,9-tetradeoxy-L-glycero-L-manno-nonulosonic acid", is a nine-carbon α-keto acid. Its structure is shown in FIG. 1. The recombinant cell used for production of Pse comprises genes encoding PseB, PseC, PseH, PseG, and PseI enzyme function. By the term "encoding Pse[ ] enzyme function", also referred to herein as "Pse genes", it is meant that the genes encode an enzyme with a function equivalent to that of Pse[ ]; these enzyme notations and their functions are described in Table 1 and FIG. 2. The Pse genes inserted into the recombinant cell may be from any suitable source, including any biological source capable of producing pseudaminic acid; for example, and without wishing to be limiting in any manner, these genes may be from *Aeromonas punctata, A. hydrophila, P. aeruginosa, Sinorhizobium meliloti, Rhizobium* sp. NGR234, *H. pylori, C. jejuni, C. coli*, or any other suitable source. The recombinant cell for production of Pse also comprises genes encoding GlcNAc-6-P mutase and GlcNAc-1-P uridyltransferase (Table 2 and FIG. 2). The GlcNAc-6-P mutase and GlcNAc-1-P uridyltransferase genes may be from any suitable source; as would be known to those of skill in the art, many biological sources comprise GlcNAc-6-P mutase or GlcNAc-1-P uridyltransferase genes, and any of these may be used in the present invention. For example, and without wishing to be limiting in any manner, the genes may be from *S. cerevisiae, Candida albicans, Homo sapiens, Drosophila melanogaster*, or any other suitable source.

Additionally, the recombinant cell used for production of Pse comprises inactivated GlcNAc-6-P deacetylase gene, described in Table 2. Optionally, the recombinant cell used for production of Pse may further comprise an inactivated sialic acid transporter gene, and/or an inactivated sialic acid aldolase gene. As would be understood by those of skill in the art, the source of the inactivated genes will be dependent on the type of recombinant cell used. By the term "inactivated", it is meant that the gene does not encode a functional product. The gene may be rendered inactive by any suitable method known in the art, for example, but not limited to partial or complete deletion of the gene DNA, or insertion of additional DNA within the gene (resulting in the inability to produce a functional gene product or enzyme).

TABLE 2

Genes manipulated in recombinant cells (*E. coli*) for the production of pseudaminic acid, legionaminic acid, or respective biosynthetic precursors (in addition to those of Table 1).

| Gene Description | Catalytic Activity or Function of Protein |
| --- | --- |
| Deletions or Inactivations | |
| sialic acid transporter | Transport of sialic acid across biological membranes |
| sialic acid aldolase | Sialic acid (Neu5Ac) → N-acetyl-D-mannosamine (ManNAc) + pyruvate |
| GlcNAc-6-P deacetylase | N-acetyl-D-glucosamine 6-phosphate → D-glucosamine 6-phosphate + acetate |
| Additions | |
| GlcNAc-6-P mutase | Interconverts N-acetyl-D-glucosamine 6-phosphate and N-acetyl-α-D-glucosamine 1-phosphate |
| GlcNAc-1-P uridyltransferase | UTP + N-acetyl-α-D-glucosamine 1-phosphate → pyrophosphate + UDP-N-acetyl-α-D-glucosamine (UDP-GlcNAc) |

In one specific, non-limiting example, the recombinant cell for production of pseudaminic acid is an *E. coli* cell comprising an inactivated sialic acid transporter gene (nanT; encoding SEQ ID NO:14), an inactivated sialic acid aldolase gene (nanA; encoding SEQ ID NO:15), and an inactivated GlcNAc-6-P deacetylase gene (nagA; encoding SEQ ID NO:16); the recombinant cell also comprises a gene encoding *H. pylori* PseB (SEQ ID NO:1), a gene encoding *H. pylori* PseC (SEQ ID NO:2), a gene encoding *H. pylori* PseH (SEQ ID NO:3), a gene encoding *H. pylori* PseI (SEQ ID NO:4), a gene encoding *C. jejuni* PseG (SEQ ID NO:5), a gene encoding *S. cerevisiae* GlcNAc-6-P mutase (Agm1; SEQ ID NO:12), and the *S. cerevisiae* gene uap1 (encoding a GlcNAc-1-P uridyltransferase; SEQ ID NO:13); one specific, non-limiting example is construct BRL04/pBRL178/pBRL175, described herein. In another non-limiting example, the recombinant strain is IDAC deposit No. 060411-02.

Legionaminic acid, also referred to herein as "Leg", "Leg5Ac7Ac", or "5,7-diacetamido-3,5,7,9-tetradeoxy-D-glycero-D-galacto-nonulosonic acid", is also a nine-carbon α-keto acid. Its structure is shown in FIG. 1. The recombinant cell for production of Leg comprises genes encoding PglF, PglE, PglD, LegG, and LegI enzyme function. By the term "encoding Pgl[ ]/Leg[ ] enzyme function", also referred to herein as "Pgl[ ]/Leg[ ] genes", it is meant that the genes encode an enzyme with a function equivalent to that of Pgl[ ]/Leg[ ]; these enzyme notations and their functions are described in Table 1 and FIG. 2. The Leg or Pgl genes inserted into the recombinant cell may be from any suitable source, including any biological source capable of producing legionaminic acid; for example, and without wishing to be limiting in any manner, the genes may be from *C. jejuni, C. coli, L. pneumophila, Clostridium botulinum, E. coli* O161, *Acinetobacter baumannii, Pseudomonas fluorescens, Vibrio salmonicida, V. alginolyticus, V. parahaemolyticus*, or any other suitable source. The recombinant cell for production of Leg also comprises genes encoding GlcNAc-6-P mutase and GlcNAc-1-P uridyltransferase (Table 2 and FIG. 2). The GlcNAc-6-P mutase and GlcNAc-1-P uridyltransferase genes may be from any suitable source; as would be known to those of skill in the art, many biological sources comprise GlcNAc-6-P mutase or GlcNAc-1-P uridyltransferase genes, and any of these may be used in the present invention. For example, and without wishing to be limiting in any manner, the genes may be from *S. cerevisiae, C. albicans, Homo sapiens, Drosophila melanogaster*, or any other suitable source.

Additionally, and similarly to the recombinant cell used for production of Pse, the recombinant cell used for production of Leg comprises an inactivated GlcNAc-6-P deacetylase gene, described in Table 2. As would be understood by those of skill in the art, the source of the inactivated genes will be dependent on the type of recombinant cell used. Optionally, the recombinant cell for producing Leg may either have an inactivated sialic acid transporter gene, an inactivated sialic acid aldolase gene, an inactivated ManNAc-6-P epimerase gene (for example, nanE), an inactivated undecaprenyl-P/UDP-GlcNAc transferase gene (for example, wecA), or a combination thereof. NanE may be responsible for depletion of intermediates in the Leg biosynthetic pathway (specifically 6-deoxy-MandiNAc), while WecA may be responsible for the depletion of intermediates in the Leg biosynthetic pathway (specifically UDP-BacdiNAc).

In a specific, non-limiting example, the recombinant cell for production of legionaminic acid is an *E. coli* cell comprising an inactivated sialic acid transporter gene (nanT; encoding SEQ ID NO:14), an inactivated sialic acid aldolase gene (nanA; encoding SEQ ID NO:15), an inactivated GlcNAc-6-P deacetylase gene (nagA; encoding SEQ ID NO:16), a gene encoding *C. jejuni* PglF (SEQ ID NO:6), a gene encoding C. jejuni PglE (SEQ ID NO:7), a gene encoding C. jejuni PglD (SEQ ID NO:8), a gene encoding C. jejuni LegI (SEQ ID NO:9), a gene encoding L. pneumophila LegG (SEQ ID NO:11), a gene encoding S. cerevisiae GlcNAc-6-P mutase (Agm1; SEQ ID NO:12), and the S. cerevisiae gene uap1 (encoding a GlcNAc-1-P uridyltransferase; SEQ ID NO:13). Optionally, the recombinant cell further comprises an inactivated ManNAc-6-P epimerase gene (nanE; encoding SEQ ID NO:17), an inactivated undecaprenyl-P/UDP-GlcNAc transferase gene (wecA; encoding SEQ ID NO:18), or a combination thereof.

The present invention further provides a cell-based fermentation method for the production of pseudaminic acid, comprising growing the recombinant cell as described above (for the production of Pse) and recovering the produced pseudaminic acid.

Similarly, the present invention provides a cell-based fermentation method for the production of legionaminic acid, comprising growing the recombinant cell as described above (for the production of Leg) and recovering the produced legionaminic acid.

By the term "cell-based fermentation method", it is meant that microorganisms are used in a fermentation process; in the present case, the microorganisms are the recombinant cells of the present invention. The fermentation process may occur under aerobic or anaerobic conditions; specific methods and conditions for cell-based fermentation may vary based on the type of recombinant cell, and are well-known in the art. The fermentation process may also be conducted as either a batch or a continuous process. In the batch process, the recombinant cells are mixed in an aqueous suspension of growth medium and optionally supplements, and placed under an atmosphere that includes or excludes oxygen. In a continuous mode, the aqueous suspension of the recombinant cells and medium is circulated through the fermentor at a constant flow rate, such that the volume in the fermentation vessel is constant; at steady state, the growth rate of the cells is equal to the dilution rate.

The final product, legionaminic acid or pseudaminic acid, may be recovered from the culture medium or cell lysates by any suitable method known in the art. For example, and without wishing to be limiting in any manner, the legionaminic acid or pseudaminic acid may be recovered by conventional chromatography utilizing, for example, preparative fast performance liquid chromatography or high performance liquid chromatography (FPLC/HPLC) instruments, or recovered by precipitation and/or recrystallization approaches. In a batch fermentation process, the final product may be recovered at the end of the process; in a continuous process, the final product may be recovered continuously or at various time points.

The present invention also provides recombinant cells and methods for production of legionaminic and pseudaminic acid precursors, also referred to herein as UDP-2,4-diacetamido-2,4,6-trideoxy hexoses (UDP-DATDHs). Specifically, the present invention provides a recombinant cell for the production of UDP-DATDHs such as the pseudaminic acid biosynthetic precursor UDP-2,4-diacetamido-2,4,6-trideoxy-β-L-altropyranose (UDP-6-deoxy-AltdiNAc) and the legionaminic acid biosynthetic precursor UDP-2,4-diacetamido-2,4,6-trideoxy-α-D-glucopyranose (UDP-BacdiNAc).

UDP-2,4-diacetamido-2,4,6-trideoxy-β-L-altropyranose, also referred to herein as UDP-6-deoxy-AltdiNAc, is a pseudaminic acid biosynthetic precursor; it can be converted to Pse by the actions of PseG and PseI enzymes. The recombinant cell for production of UDP-6-deoxy-AltdiNAc comprises genes encoding PseB enzyme function, a gene encoding PseC enzyme function, and a gene encoding PseH enzyme function (Table 1 and FIG. 2); the recombinant cell for producing UDP-6-deoxy-AltdiNAc also comprises a gene encoding GlcNAc-6-P mutase and a gene encoding a GlcNAc-1-P uridyltransferase (Table 2 and FIG. 2). The source of the Pse genes described above may be from any suitable source, including a biological source capable of producing UDP-6-deoxy-AltdiNAc. For example, and without wishing to be limiting in any manner, the genes may be from H. pylori, C. jejuni, or any other suitable source. The source of the GlcNAc-6-P mutase gene, and the GlcNAc-1-P uridyltransferase genes inserted into the recombinant cell for the production of UDP-6-deoxy-AltdiNAc are as described above for the recombinant cell for the production of pseudaminic acid.

Additionally, the recombinant cell used for production of UDP-6-deoxy-AltdiNAc comprises an inactivated GlcNAc-6-P deacetylase gene, described in Table 2. Optionally, the recombinant cell used for production of UDP-6-deoxy-AltdiNAc comprises an inactivated sialic acid transporter gene, and/or an inactivated sialic acid aldolase gene. As would be understood by those of skill in the art, the source of the inactivated genes will be dependent on the type of recombinant cell used.

In a specific, non-limiting example, the recombinant cell for production of UDP-6-deoxy-AltdiNAc is an E. coli cell comprising an inactivated sialic acid transporter gene (nanT; encoding SEQ ID NO:14), an inactivated sialic acid aldolase gene (nanA; encoding SEQ ID NO:15), an inactivated GlcNAc-6-P deacetylase gene (nagA; encoding SEQ ID NO:16), a gene encoding H. pylori PseB (SEQ ID NO:1), a gene encoding H. pylori PseC (SEQ ID NO:2), a gene encoding H. pylori PseH (SEQ ID NO:3), a gene encoding S. cerevisiae GlcNAc-6-P mutase (Agm1; SEQ ID NO:12), and the S. cerevisiae gene uap1 (encoding a GlcNAc-1-P uridyltransferase; SEQ ID NO:13); one specific, non-limiting example is construct BRL04/pBRL178/pBRL151, described herein.

UDP-2,4-diacetamido-2,4,6-trideoxy-α-D-glucopyranose, also referred to herein as UDP-BacdiNAc, is a legionaminic acid biosynthetic precursor; UDP-BacdiNAc can be converted to Leg by the actions of LegG and LegI enzymes. The recombinant cell for production of UDP-BacdiNAc comprises genes encoding PglF, PglE, and PglD enzyme functions (Table 1 and FIG. 2); the recombinant cell for producing UDP-BacdiNAc also comprises a gene encoding GlcNAc-6-P mutase and a gene encoding a GlcNAc-1-P uridyltransferase (Table 2 and FIG. 2). The source of the Pgl genes described above may be from any suitable source, including a biological source capable of producing UDP-BacdiNAc. For example, and without wishing to be limiting in any manner, the genes may be from C. jejuni, L. pneumophila, or any other suitable source. The source of the GlcNAc-6-P mutase gene and the GlcNAc-1-P uridyltransferase gene inserted into the recombinant cell for the production of UDP-BacdiNAc are as described above for the recombinant cell for the production of legionaminic acid.

Additionally, the recombinant cell used for production of UDP-BacdiNAc comprises an inactivated GlcNAc-6-P deacetylase gene, described in Table 2. Optionally, the recombinant cell for producing UDP-BacdiNAc comprises an inactivated sialic acid transporter gene, and/or an inactivated sialic acid aldolase gene, and/or an inactivated undecaprenyl-P/UDP-GlcNAc transferase gene. As would be understood by those of skill in the art, the source of the inactivated genes will be dependent on the type of recombinant cell used.

In a specific, non-limiting example, the recombinant cell for production of UDP-BacdiNAc is an *E. coli* cell comprising an inactivated sialic acid transporter gene (nanT; encoding SEQ ID NO:14), an inactivated sialic acid aldolase gene (nanA; encoding SEQ ID NO:15), and an inactivated GlcNAc-6-P deacetylase gene (nagA; encoding SEQ ID NO:16); the recombinant cell also comprises a gene encoding *C. jejuni* PglF (SEQ ID NO:6), a gene encoding *C. jejuni* PglE (SEQ ID NO:7), and a gene encoding *C. jejuni* PglD (SEQ ID NO:8), a gene encoding *S. cerevisiae* GlcNAc-6-P mutase (Agm1; SEQ ID NO:12), and the *S. cerevisiae* gene uap1 (encoding a GlcNAc-1-P uridyltransferase; SEQ ID NO:13). The bacterial cell may additionally comprise an inactivated undecaprenyl-P/UDP-GlcNAc transferase gene (wecA; encoding SEQ ID NO:18); one specific, non-limiting example is construct BRL04/pBRL178/pBRL152, described herein. In another non-limiting example, the recombinant strain is IDAC deposit No. 060411-01.

The present invention also provides a cell-based fermentation method for the production of UDP-2,4-diacetamido-2,4,6-trideoxy-β-L-altropyranose (UDP-6-deoxy-AltdiNAc), comprising growing the recombinant cell as described above and recovering the produced UDP-6-deoxy-AltdiNAc.

The present invention further provides a cell-based fermentation method for the production of UDP-2,4-diacetamido-2,4,6-trideoxy-α-D-glucopyranose (UDP-BacdiNAc), comprising growing the recombinant cell as described above and recovering the produced UDP-BacdiNAc.

The enzymes and genes described in the above bacterial cells for the production of precursor compounds are as described previously above. Similarly, conditions for the methods just described are as indicated above for the production of the final products. Methods for recovering the products are as described herein.

The precursors, UDP-6-deoxy-AltdiNAc and UDP-BacdiNAc, obtained using the recombinant cells and methods above, may be converted to pseudaminic acid and legionaminic acid, respectively. Methods for conversion of these precursors to the final product are well known in the art. For example, UDP-6-deoxy-AltdiNAc may be converted to pseudaminic acid by incubation in a reaction vessel comprising a UDP-sugar hydrolase (PseG), a pseudaminic acid synthase (PseI), and phosphoenolpyruvate (PEP) or pyruvate. Alternatively, UDP-6-deoxy-AltdiNAc sugar could be converted to 6-deoxy-AltdiNAc with PseG, which may be chemically modified as described by Lee et al. (2010), to produce pseudaminic acid. As well, UDP-6-deoxy-AltdiNAc may be converted to 6-deoxy-AltdiNAc by chemical methods (such as heat or acidic treatment), and then converted to pseudaminic acid with PseI and PEP/pyruvate or the chemical methods described above. Similarly, UDP-BacdiNAc may be converted to legionaminic acid by incubating it in a reaction vessel comprising a UDP-sugar hydrolase and 2-epimerase (LegG), a legionaminic acid synthase (LegI) or sialic acid aldolase, and phosphoenolpyruvate (PEP) or pyruvate. Alternatively, the UDP-BacdiNAc may be converted to Leg by chemi-enzymatic methods similar to above (Tsvetkov et al., 2001).

Optionally, the Pse and Leg sugars produced by the methods described herein may be further converted to respective CMP-activated sugars with the CMP-pseudaminic acid synthetase (PseF; Schoenhofen et al, 2006a) and CMP-legionaminic acid synthetase (LegF; Schoenhofen et al, 2009), respectively. PseF catalyzes the reaction [CTP+pseudaminic acid→CMP-pseudaminic acid+pyrophosphate], whereas LegF catalyzes the reaction [CTP+legionaminic acid→CMP-legionaminic acid+pyrophosphate]. The conversion to CMP-sugars may be accomplished by any suitable method in the art, for example either by co-expression within recombinant cells (i.e. PseBCHGIF or PglFED/LegGIF strains), mixing of separate recombinant cells (i.e. PseBCHGI+PseF, or PglFED/LegGI+LegF), or by in vitro synthesis after their isolation (Pse or Leg) using methods known to those skilled in the art. The PseF and LegF enzymes may be from any suitable source; for example, and without wishing to be limiting in any manner, the genes may be from *H. pylori, C. jejuni, C. coli, P. aeruginosa, L. pneumophila*, or any other suitable source. Methods of producing such CMP-activated sugars are encompassed by the present invention.

To produce pseudaminic acid, the complete Pse-biosynthetic pathway and UDP-GlcNAc generating enzymes Agm1 and Uap1 were introduced into an *E. coli* strain (BRL02) previously engineered for the synthesis of sialic acid (Example 3). This system failed to produce significant levels of Pse or Pse-pathway intermediates. The extremely low productivity was attributed to the degradation of the Agm1/Uap1/PseBCHGI-pathway substrate, GlcNAc-6-P, via NagA (GlcNAc-6-P deacetylase). Therefore, the pseBCHGI and agm1/uap1 genes were introduced into the ΔnagA *E. coli* strain BRL04 (Example 3). However, co-transformation of the PseBCHGI pathway and Agm1/Uap1 proteins as a hepta-cistronic operon, encoded on a single vector (pBRL179), into the ΔnagA strain BRL04 failed to produce viable clones on every attempt. The pseBCHGI-agm1-uap1 operon is controlled by a T7 promoter, and it is widely accepted that leaky expression results from T7 promoters (Studier et al, 1990). The failure to co-transform the Pse-biosynthetic pathway and Agm1/Uap1 proteins into the ΔnagA strain BRL04 was due to a toxicity associated with the leaky expression of the pse-BCHGI/agm1/uap1 genes. Independent transformations of either the pseBCHGI or agm1/uap1 genes were successful in generating viable clones, which indicated that neither pathway alone is toxic in the ΔnagA strain. Only a combination of both sets of genes was required for toxicity (Example 3). By splitting the hepta-cistronic PseBCHGI/Agm1/Uap1 system into two operons, pseBCHGI and agm1/uap1, on two separate, T7-controlled expression vectors (pBRL175 and pBRL178) with different replication origins, viable BRL04/pseBCHGI/agm1/uap1 clones were generated. Analysis of cell-free culture broth from these BRL04/pseBCHGI/agm1/uap1 cells (i.e. two operon system above) in a glycerol/GlcNAc-batch fermentation by LCMS ESI$^+$ (FIG. 7A) indicated pseudaminic acid production (Example 3).

The sub-optimal production of the Pse product and pathway intermediates in some engineered strains (BRL02, BL21 (DE3), BRL25; Examples 3 and 6) suggested that either the acetyl-CoA levels were suboptimal due to an additional N-acetylation required relative to sialic acid biosynthesis; that the intermediates in the Pse-biosynthetic pathway were being consumed by undesirable intracellular glycosylation reactions; or that intermediates were degraded by unidentified mechanisms. Removal of all non-essential glycosylation reactions in the engineered *E. coli* strain (BRL25) did not have an effect on the production of pseudaminic acid (Example 6).

The only dissimilation pathway in *E. coli* K-12 for 2-acetamido sugars (Plumridge & Vimr, 1999) involves a highly specific process that includes a deacetylase, NagA, and a deaminase, NagB (Plumridge & Vimr, 1999). The deacetylase, NagA, removes the acetate at C2 of N-acetyl glucosamine-6-phosphate (GlcNAc-6-P) to generate glucsosamine-6-phosphate (GlcN-6-P); NagB then deaminates GlcN-6-P into fructose-6-phosphate, which then enters central metabolism. This pathway may be responsible for catabolizing the Pse-biosynthetic pathway intermediates, which have the same configuration at C2, thus preventing the production of pseudaminic acid. Only when the GlcNAc-6-P deacetylase, NagA, was deleted was Pse readily produced (Example 3). It is therefore possible that the native *E. coli* pathway for the degradation of N-acetylglucosamine is in fact able to catabolize 2-acetamido-6-deoxy hexoses such as 2,4-diacetamido-2,4,6-trideoxy-L-altropyranose (6-deoxy-AltdiNAc).

The present invention will be further illustrated in the following examples. However, it is to be understood that these examples are for illustrative purposes only and should not be used to limit the scope of the present invention in any manner.

Example 1

Construction of Recombinant Pathway for Pseudaminic Acid, UDP-6-Deoxy-AltdiNAc, and UDP-BacdiNAc Biosynthesis Plasmids encoding the *H. pylori* pseB, pseC, pseH and pseI genes, and the *C. jejuni* pseG gene were provided by the Institute for Biological Sciences, National Research Council (Ottawa, Ontario, Canada). The plasmids were used as templates for PCR with the primers given in Table 3. Initial constructions of *H. pylori* pseB, pseC, pseH and pseG genes (in a pseBCHGI operon) examined via Western blot of cell lysates showed that the *H. pylori* PseB, PseC and PseH were successfully expressed but not PseG (data not shown). Therefore, the *C. jejuni* PseG was cloned and used in place of *H. pylori* PseG.

The pglF, pglE and pglD genes were amplified from *C. jejuni* (ATCC® 700819-5) genomic DNA using primers also shown in Table 3.

mid pKH22 (Lundgren and Boddy, 2007; Table 7). The subcloning of genes and construction of recombinant expression vectors described in this and following Examples was done using standard molecular biology techniques (Erbel et al, 2003).

A full pseudaminic acid biosynthetic pathway was constructed using genes encoding the proteins PseB (HP0840; SEQ ID NO:1), PseC (HP0366; SEQ ID NO:2), PseH (HP0327; SEQ ID NO:3), and PseI (HP0178; SEQ ID NO:4) from *H. pylori* and PseG (Cj1312; SEQ ID NO: 5) from *C. jejuni*. This set of enzymes was shown to synthesize Pse from UDP-GlcNAc in vitro (Schoenhofen et al, 2006a). The pseBCHGI operon was constructed by sequentially cloning the Xba I-Avr II fragment of the targeted downstream gene(s) into the Avr II of the parental vector, yielding a low-copy expression vector and arranged into a penta-cistronic operon, controlled by a single T7 promoter (pBRL175; Table 4).

The UDP-6-deoxy-AltdiNAc biosynthetic pathway was constructed using genes encoding the proteins PseB (HP0840; SEQ ID NO:1), PseC (HP0366; SEQ ID NO:2), and PseH (HP0327; SEQ ID NO:3) from *H. pylori*. This set of enzymes was shown to synthesize UDP-6-deoxy-AltdiNAc from UDP-GlcNAc in vitro (Schoenhofen et al, 2006a; Schoenhofen et al, 2006b). Construction of the pseBCH operon was achieved by sequentially cloning the Xba I-Avr II fragment of the targeted downstream gene(s) into the Avr II of the parental vector, resulting in a low-copy expression vector and arranged into a tri-cistronic operon, controlled by a single T7 promoter (pBRL151, Table 4).

The UDP-BacdiNAc biosynthetic pathway was constructed using genes encoding the proteins PglF (Cj1120c SEQ ID NO:6), PglE (Cj1121c SEQ ID NO:7), and PglD (Cj1123c SEQ ID NO:8) from *C. jejuni*. This set of enzymes was shown to synthesize UDP-BacdiNAc from UDP-GlcNAc in vitro (Schoenhofen et al, 2006b; Oliver et al, 2006). Construction of the pglFED operon was achieved by

TABLE 3

Forward (f) and reverse (r) primers used for amplification of pse and pgl genes, shown with restriction sites. Primers (m1, m2) used for the mutagenesis of pseB to remove internal EcoRI site are given.

| | | | | |
|---|---|---|---|---|
| pseB | f-gcagcatatgccaaatcatcaaaacatgctag | SEQ ID NO: 19 | Nde I |
| | r-gcagg*aattc*tcataataatttcaacaaatcatcaggctc | SEQ ID NO: 20 | EcoRI |
| | m1-ccatttagccctagagttcgaagacttttcatcattcagccc | SEQ ID NO: 21 | |
| | m2-gggctgaatgatgaaaaagtcttcgaactctagggctaaatgg | SEQ ID NO: 22 | |
| pseC | f-gcagcatatgaaagagtttgcttatagcgag | SEQ ID NO: 23 | Nde I |
| | r-gcagg*aattc*tcattctattttaaaactctcaaaag | SEQ ID NO: 24 | EcoR I |
| pseH | f-gcag*catatg*aaaaaaaattattcttataaaaatatccaagcgattg | SEQ ID NO: 25 | Nde I |
| | r-gcagg*aattc*ctaaagttttagaagagattgatcattatatc | SEQ ID NO: 26 | EcoR I |
| pseG | f-ggaccatatgaaagtgcttttagaagcgatagc | SEQ ID NO: 27 | Nde I |
| | r-ggacgaattctcaatacttatactccacttcataccc | SEQ ID NO: 28 | EcoR I |
| pseI | f-gcag*catatg*ttacaaccccctaaaattgtc | SEQ ID NO: 29 | Nde I |
| | r-gcagg*aattc*ctacaatgagcgttctatatcatc | SEQ ID NO: 30 | EcoR I |
| pglF | f-gcagcatatgatttttataaaagcaaaagattagca | SEQ ID NO: 31 | Nde I |
| | r-gcaggaattcttatacaccttctttattgtgtttaaattc | SEQ ID NO: 32 | EcoR I |
| pglE | f-gcagcatatgagattttttctttctcctccgcacatgggtggtaatg | SEQ ID NO: 33 | Nde I |
| | r-gcaggaattcttaagcctttatgctcttaagatcagtttga | SEQ ID NO: 34 | EcoR I |
| pglD | f-gcagcatatggcaagaactgaaaaaatttatatttatgg | SEQ ID NO: 35 | Nde I |
| | r-gcaggaattcttacatcctttttgcaggtactcc | SEQ ID NO: 36 | EcoR I |

The PCR products were cloned into various plasmids, including pCR-Blunt (Invitrogen, Carlsbad, Calif.) and plassequentially cloning the Xba I-Avr II fragment of the targeted downstream gene(s) into the Avr II of the parental vector, resulting in a low-copy expression vector and arranged into a tri-cistronic operon, controlled by a single T7 promoter (pBRL152, Table 4).

Resulting plasmids, listed in Table 4, may be used for the biosynthesis of pseudaminic acid (Pse), legionaminic acid (Leg) and their precursors UDP-6-deoxy-AltdiNAc and UDP-BacdiNAc, respectively.

TABLE 4

Plasmids used for the production of UDP-GlcNAc, pseudaminic acid (Pse), UDP-2,4-diacetamido-2,4,6-trideoxy-α-D-glucopyranose (UDP-BacdiNAc) and UDP-2,4-diacetamido-2,4,6-trideoxy-β-L-altropyranose (UDP-6-deoxy-AltdiNAc)

| Plasmid | Operon | Biosynthesized Metabolite | |
|---|---|---|---|
| pBRL179 | pseBCHGI-agm1-uap1 | Pse | See Example 3 |
| pBRL175 | pseBCHGI | Pse | See Example 3 |
| pBRL151 | pseBCH | UDP-6-deoxy-AltdiNAc | See Example 5 |
| pBRL152 | pglFED | UDP-BacdiNAc | See Example 5 |
| pBRL178 | agm1-uap1 | UDP-GlcNAc | See Example 3 |

Example 2

Cloning of a UDP-GlcNAc Biosynthetic Pathway

The Pse-biosynthetic pathway diverges from *E. coli* metabolism at the key branch point UDP-GlcNAc, the synthesis of which is tightly regulated by homeostatic mechanisms (Plumbridge et al, 1993). To circumvent the dependency of Pse/Leg or UDP-6-deoxy-AltdiNAc/UDP-BacdiNAc production from UDP-GlcNAc supplied only by homeostasis, a foreign, yeast-derived UDP-GlcNAc biosynthetic pathway was co-expressed with the Pse or UDP-6-deoxy-AltdiNAc/UDP-BacdiNAc biosynthetic pathways.

The genes encoding the enzymes for a GlcNAc-6-P mutase (Hofmann et al, 1994), Agm1 (SEQ ID NO:12), and a GlcNAc-1-P uridyltransferase (Mio et al, 1998), Uap1 (SEQ ID NO:13), were cloned from *Saccharomyces cerevisiaie*. For *E. coli*, exogenously-fed GlcNAc is taken up by PTS-transporters, i.e., ManXYZ and/or NagE (GlcNAc-inducible), to generate intracellular GlcNAc-6-P, which can only be degraded into Fru-6-P in wild-type *E. coli*. Expression of the non-native Agm1/Uap1 pathway enabled GlcNAc-6-P to be directly converted to UDP-GlcNAc, bypassing *E. coli* central metabolism and generating higher pools of UDP-GlcNAc for Pse, Leg, UDP-BacdiNAc, and UDP-6-deoxy-AltdiNAc production.

The agm1 (GlcNAc-6-P mutase) and uap1 (GlcNAc-1-P uridyltransferase) from *S. cerevisiae* were previously cloned into the expression vector pKH22 as a bi-cistronic operon controlled by a T7-promoter, thus generating the plasmid pBRL80 (Lundgren, 2010). This system was highly productive in converting exogenously supplied GlcNAc into UDP-GlcNAc (Lundgren, 2010).

The Xba I/Avr II agm1-uap1 fragment from pBRL80 was sub-cloned into either the Avr II site of pBRL175 (pseBCHGI) or the Xba I site of pKH61 (Lundgren, 2010) to generate plasmids pBRL179 and pBRL178, respectively (Lundgren, 2010). The vector pBRL179 encoded all the necessary genes for channelling GlcNAc into Pse production. In contrast, the pBRL178 supplied only the agm1-uap1 genes but could be readily co-expressed with the plasmid-encoded pathways for UDP-6-deoxy-AltdiNAc (pseBCH on pBRL151), Pse (pseBCHGI on pBRL175), or UDP-BacdiNAc (pglFED on pBRL152), or Leg.

Example 3

Pseudaminic Acid Production from *E. Coli*

For initial Pse production experiments, the PseBCHGI pathway was expressed in the commercially available, industrially-friendly *E. coli* BL21(DE3) strain. Chemical transformation of plasmids into cells was performed using art-known methods. Because there was no known Pse-specific aldolase or degradation pathway for 2-acetamido-6-deoxy sugars encoded in the *E. coli* genome (Lewis et al, 2009), *E. coli* BL21(DE3) served as a desirable host for Pse production due to its robustness in gene expression. However, the BL21 (DE3)/PseBCHGI strain failed to produce any detectable Pse from either glycerol or glucose batch fermentation (data not shown). Expression of the non-native pseBCHGI genes was not an issue, because the Pse-biosynthetic proteins were detected by Western blots of production-culture cell lysates derived from both minimal and complex media (data not shown).

The Pse-biosynthetic pathway along with the Agm1 and Uap1 genes (pBRL179, Example 1) were transformed into and co-expressed in the nanT⁻ nanA⁻ *E. coli* strain BRL02 (Table 6) using method known in the art; this strain was previously engineered for sialic acid production (Lundgren & Boddy, 2007). Pse production was performed using a mixed feeding strategy of glycerol/GlcNAc batch fermentations in shake-flasks. Glycerol supplied the cells with energy and biosynthetic precursors whereas GlcNAc fed into UDP-GlcNAc synthesis for Pse production.

Briefly, starter cultures were grown in 1 mL of LB media, supplemented with the necessary antibiotics, at 37° C., 200 rpm, for 18 h. A 20 mL F2 minimal media (in 250-mL shake-flask), supplemented with the necessary antibiotics, 0.25% casitone and 1% (v/v) glycerol was inoculated with 0.2 mL of starter culture. Production cultures were grown at 37° C., 200 rpm, until an $OD_{600}$ of 0.5 was reached. At this point, pseudaminic acid production was induced with 0.2 mM IPTG (final concentration), and the incubation temperature was lowered to 30° C. Production cultures were grown for 72 h and supplemented with 0.6% (v/v) glycerol at 0, 12 and 36 h post induction. At 0, 18 and 36 h post induction, doses of 0.2% GlcNAc were added for pseudaminic acid biosynthesis/production.

Expression of the hepta-cistronic operon of pBRL179 in *E. coli* strain BRL02 produced a trace amount of Pse with m/z of 317 (M−OH), 335 (M+H), and 357 (M+Na), see FIG. 3. The extremely low productivity was attributed to the degradation of the Agm1/Uap1/PseBCHGI-pathway substrate, GlcNAc-6-P, via NagA (GlcNAc-6-P deacetylase; SEQ ID NO: 16).

Therefore, the pseBCHGI and agm1/uap1 genes in pBRL179 were introduced into the nanT nanA⁻ ΔnagA⁻ *E. coli* strain BRL04 (Table 6); chemical transformation of plasmids into cells was performed using art-known methods. Cell culture and gene expression were performed as described above. Co-transformation of the PseBCHGI pathway and Agm1/Uap1 proteins as a hepta-cistronic operon encoded on a single vector, into the ΔnagA strain BRL04 failed to produce viable clones on every attempt. The pseBCHGI-agm1-uap1 operon is controlled by a T7 promoter, and it is widely accepted that leaky expression results from T7 promoters (Studier et al, 1990). The failure to co-transform the Pse-biosynthetic pathway and Agm1/Uap1 proteins into the ΔnagA strain BRL04 was due to a toxicity associated with the leaky expression of the pseBCHGI/agm1/uap1 genes.

Independent transformations of either the pseBCHGI (in pBRL175) or agm1/uap1 genes (in pBRL178) using art-known chemical transformation methods were successful in generating viable clones (data not shown), indicating that neither pathway alone is toxic in the nanT_ nanA⁻ ΔnagA strain. Based on these results and those of Example 5, BRL04 cells were transformed with pseBCHGI (in pBRL175) and agm1/uap1 (in pBRL178) using art-known chemical transformation methods, generating viable BRL04/pseBCHGI/agm1/uap1 clones (strain BRL04/pBRL178/pBRL175). This clone was deposited with the International Depositary Authority of Canada (National Microbiology Laboratory, Public Health Agency of Canada, 1015 Arlington Street, Winnipeg, Manitoba, Canada R3E 3R2) on Apr. 7, 2011, under deposit number 060411-02.

Cell culture and gene expression were performed as described above. The pseBCHGI and agm1/uap1 genes were present on plasmids with copy numbers (replication origins) of ~20 (pMB1*) and >100 (mutated ColE1), respectively (Hayes, 2003). Under non-induced conditions, the substantially higher copy number of the uap1/agm1 operon outcompeted the pseBCHGI pathway for T7-polymerase mediated transcription. This increased the synthesis of UDP-GlcNAc but did not raise its flux through Pse biosynthesis, thus keeping Pse-pathway intermediates at non-toxic levels.

Figure 7A:
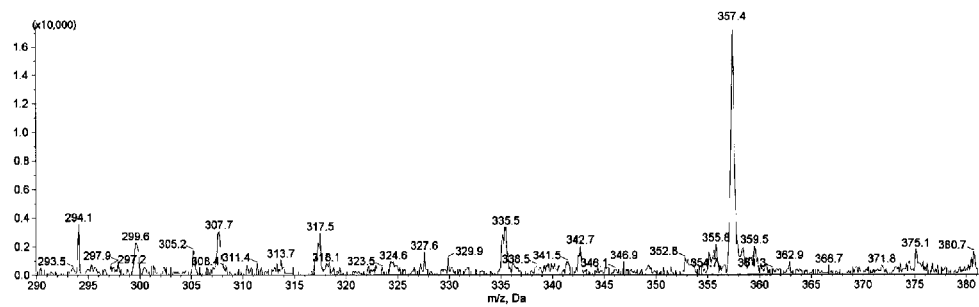
FIGS. 7A and B shows LCMS ESI$^+$ analysis of cell-free culture broth from BRL04/pseBCHGI/agm1/uap1 cells (BRL04/pBRL175/pBRL178) in a glycerol/GlcNAc-batch fermentation.

The cell-free culture broth was analyzed using a LCMS ESI$^+$ method developed herein (see Example 4). Analysis of cell-free culture broth from BRL04/pseBCHGI/agm1/uap1 cells (strain BRL04/pBRL178/pBRL175) in a glycerol/GlcNAc-batch fermentation by LCMS ESI$^+$ (FIG. 7A) showed a clear ion-extraction peak for Pse with m/z values of 317 (M−OH), 335 (M+H) and 357 (M+Na). These ion extraction peaks were not present in the negative control production culture (data not shown). To confirm that these m/z values were derived from authentic Pse, cell-free broth from the negative control culture was spiked with Pse standard. As shown in FIGS. 7A and B, the ion-extraction peak of the spiked sample was identical to the Pse produced from the BRL04/pseBCHGI/agm1/uap1 fermentation (strain BRL04/pBRL178/pBRL175). Although a quantitative Pse titer could not be determined, a rough estimate based on the inability to detect Pse standards injected at concentrations of <40 mg L$^{-1}$, would imply that Pse production was at least ≥20 mg L$^{-1}$. Quantitative determination of Pse titers can be made by analyzing pseudaminic acid from cell-free culture broth derivatized with the fluormetric reagent, 1,2-diamino-4,5-methylene dioxybenzene (DMB) by HPLC (Lewis et al, 2009; Manzi et al, 1990). This assay is widely used for sialic acid quantification and has been applied to Pse (Lewis et al, 2009).

Figure 5:
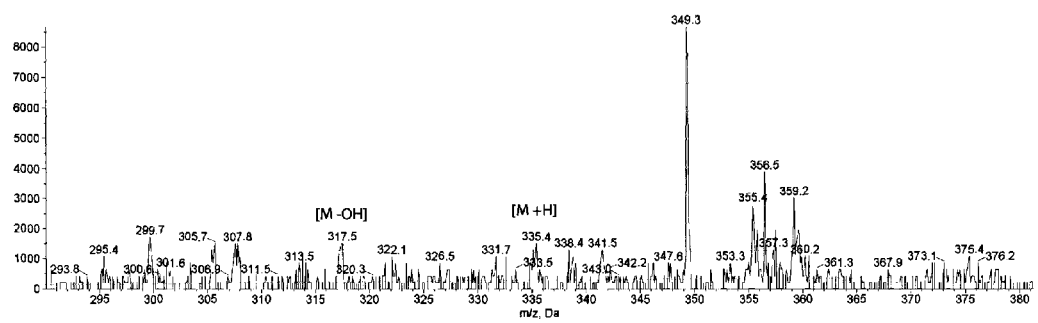
FIG. 5 shows an LCMS ESI+ spectrum of pseudaminic acid produced from *E. coli* BRL02 expressing the pseBCHGI and agm1/uap1 genes (BRL02 pBRL179) when grown on glycerol/GlcNAc. Exogenously fed GlcNAc was converted to UDP-GlcNAc by Agm1/Uap1, and the PseBCHGI pathway converted UDP-GlcNAc into pseudaminic acid as detected by LCMS ESI. Peaks at m/z of 317.5 (M−OH) and 335.4 (M+H) were observed, where M is the characteristic mass of pseudaminic acid.

The production of Pse was further optimized by increasing the acetyl-CoA pools in the nanT⁻ nanA⁻ ΔnagA E. coli strain BRL04. Unlike sialic acid, Pse biosynthesis involves a diacetamido sugar that is generated from a dedicated acetyl-CoA dependent acetyltransferase, PseH. To increase the acetyl-CoA levels in BRL04/pseBCHGI/agm1/uap1 through β-oxidation, cell culture of BRL04 transformed with pBRL175 and pBRL178 was grown and gene expression was performed as described above except that production cultures were supplemented with 0.6 mg L$^{-1}$ of palmitate. As indicated in FIG. 5, Pse was readily produced and appeared to be higher than that without palmitate addition. This suggested that acetyl-CoA may be a factor for the production of diacetamido sugars in E. coli.

Example 4

Figure 6A:
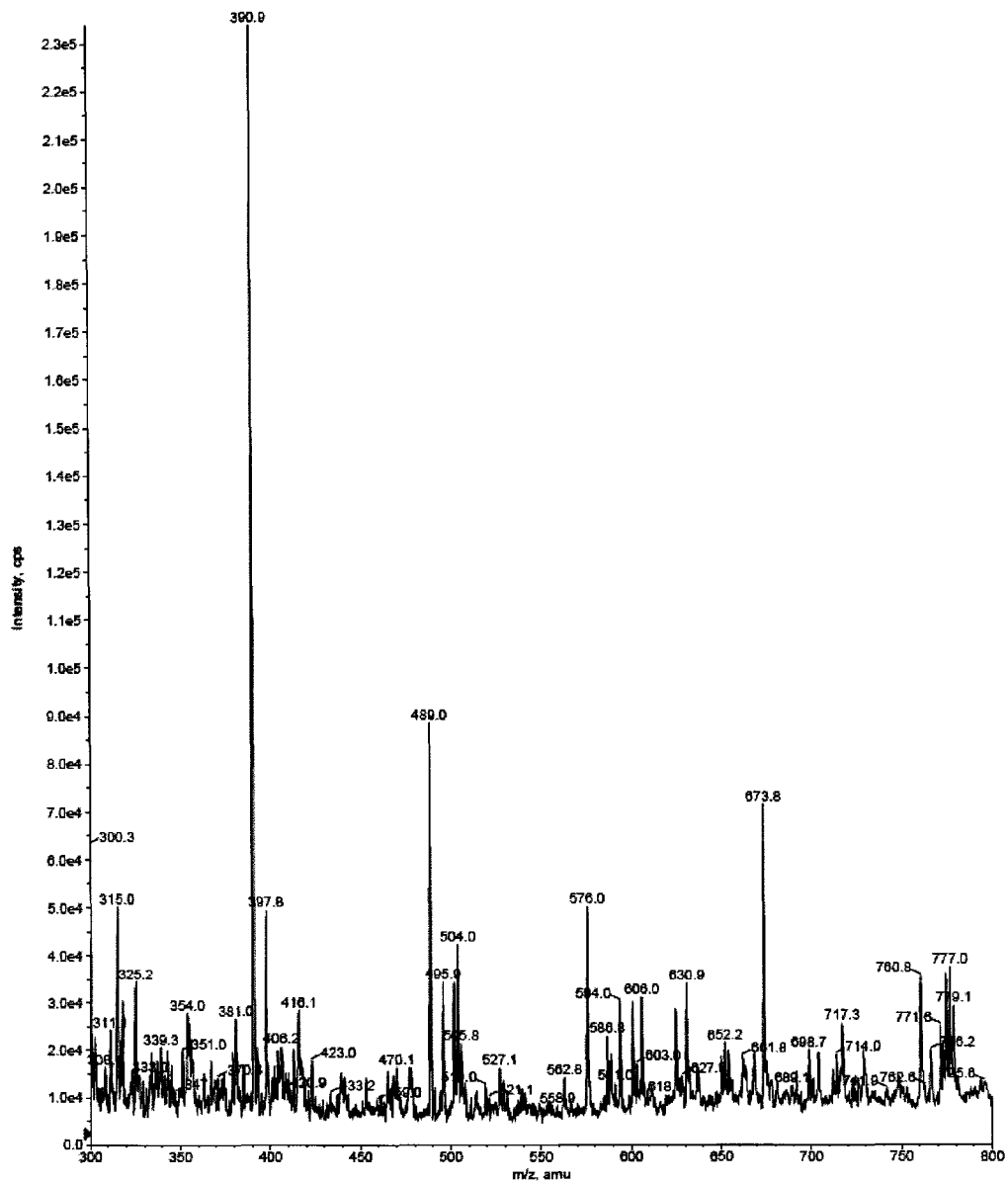
FIGS. 6A, B and C shows a CE-MS spectra (negative ion mode) of non-native UDP-activated 2,4-diacetamido-2,4,6-trideoxy hexoses (m/z 630.9) biosynthesized by *E. coli*. The enzymes involved in the biosynthesis of UDP-DATDH precursors from either the pseudaminic acid (PseBCH) or legionaminic acid (PglFED) pathway were expressed in the ΔnagA BRL04/agm1/uap1 strain. Lysates from the production cultures were analyzed by CE-MS in the negative-ion mode, and m/z peaks of 630.9 were observed from both UDP-6-deoxy-AltdiNAc (UDP-2,DATDH (UDP-2,4-diacetamido-2,4,6-trideoxy-β-L-altropyranose.
Figure 6B:
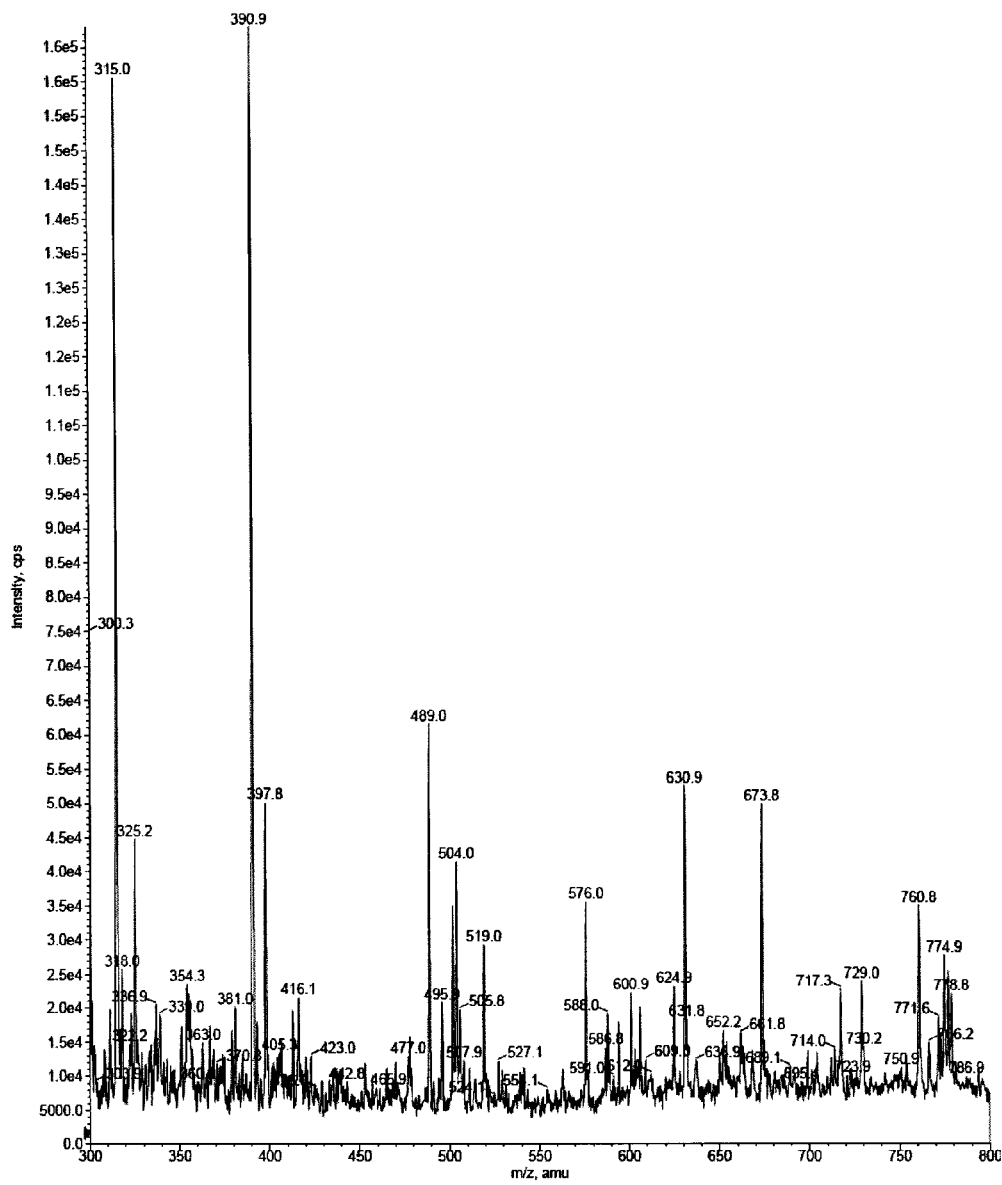
FIG. 6B) (PglFED) samples. The negative control is shown in FIG. 6C, indicating an absence of m/z peak 630.9, as expected. The strain BRL04 pBRL151/pBRL178 was used for UDP-2,4-diacetamido-2,4,6-trideoxy-β-L-altropyranose (UDP-6-deoxy-AltdiNAc) production and strain BRL04/pBRL152/pBRL178 was used for UDP-2,4-diacetamido-2,4,6-trideoxy-α-D-glucopyranose (UDP-BacdiNAc) production.
Figure 6C:
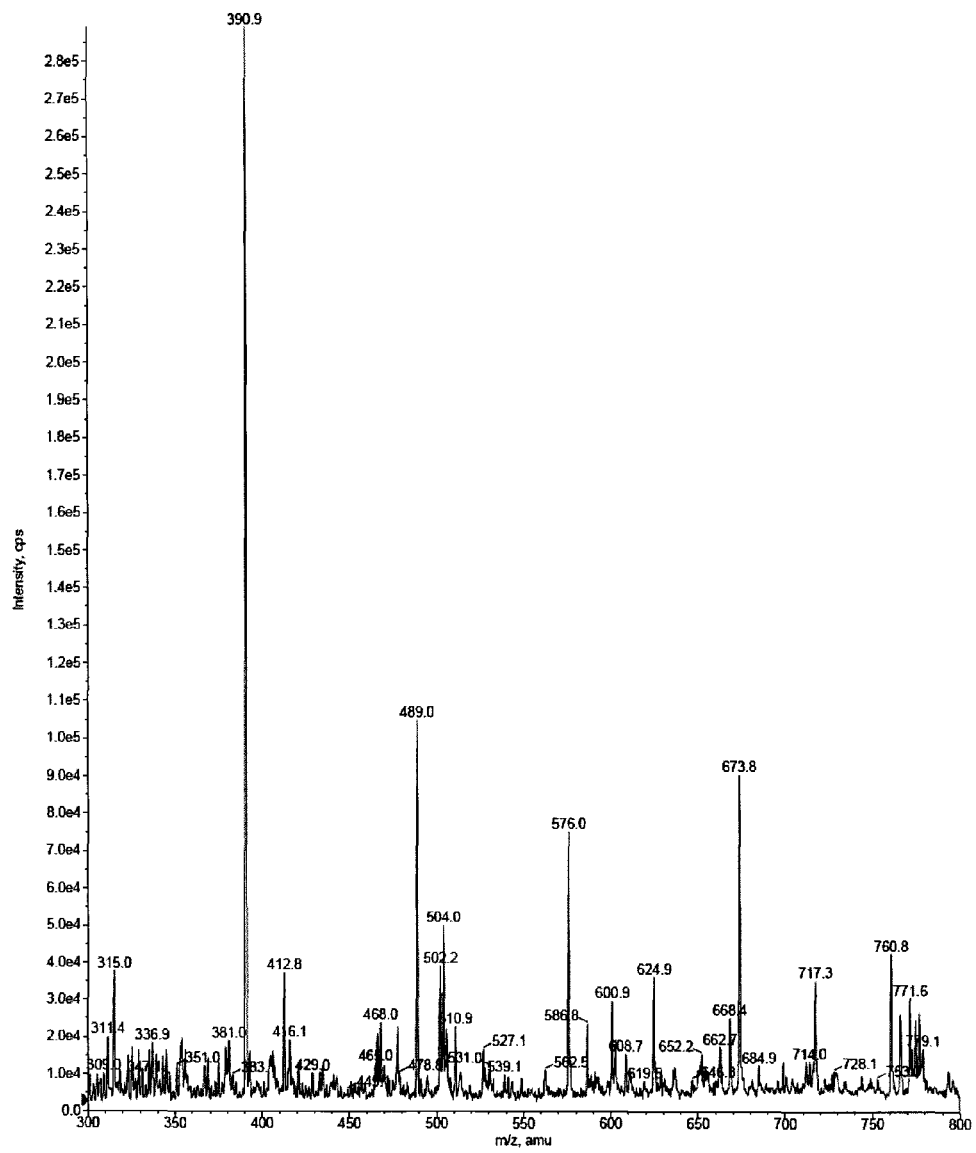

Analysis of Pseudaminic Acid and Legionaminic Acid from Cell-Free Culture Broth Via LCMS ESI$^+$ Due to the failures with Pse detection using proton NMR, a LCMS ESI$^+$ method was developed and validated to detect Pse from production cultures of Example 3 (FIG. 6).

Briefly, cell-free broth from production cultures (Example 3) were diluted 100-fold into 0.1 mL of water and analyzed by LCMS ESI$^+$ (10 µL injection volumes) on a Shimadzu LCMS 2010 A. HPLC conditions: UV detection λ=210, 254 nm, Thermo 50×4.6 mm, 3 µm, Hypercarb® HPLC column (graphitic carbon based packing), flow rate 0.15 mL/min, isocratic elution H$_2$O, 0.05% v/v formic over 20 min run time.

Example 5

Figure 7B:
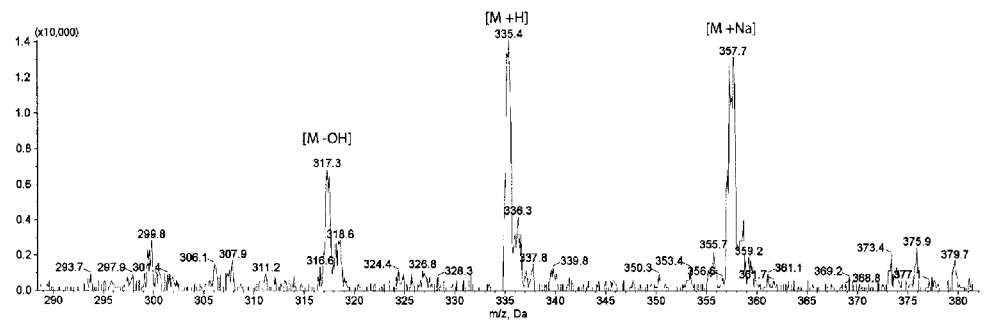

Production of UDP-Activated 2,4-diacetmido-2,4,6-Trideoxy Hexoses from E. Coli Plasmids pBRL151 (pseBCH) or pBRL152 (pglFED) (Example 1; Table 4), encoding the biosynthetic pathways for the Pse precursor UDP-6-deoxy-AltdiNAc or Leg precursor UDP-BacdiNAc (FIG. 7), respectively, were transformed with pBRL178 (agm1-uap1; Example 2; Table 4) in the nanT⁻ nanA⁻ nagA⁻ E. coli strain BRL04 (Table 6; WO 2008/097366) using art-known chemical transformation methods. The BRL04/pBRL178/pBRL173 strain was used as a negative control.

To maximize cell density for the production of the UDP-DATDHs from shake-flasks, starter cultures were scaled up in 5-fold increments. Seed cultures of BRL04/pBRL178/pBRL151 or BRL04/pBRL178/pBRL152 were grown in 1 mL LB supplemented with appropriate antibiotics at 37° C., 200 rpm, for 18 h. Afterwards, entire seed cultures were harvested, and the resulting cell pellets were re-suspended and diluted into 5 mL of LB with necessary antibiotics. Cultures were grow at 37° C., 200 rpm, for 18 h and then re-harvested. Cell pellets were used to inoculate 20 mL LB with appropriate antibiotics and grown at 37° C., 200 rpm, for 18 h. At this time, the entire 20 mL seed culture was harvested, and the cell mass was used to inoculate the production culture of 100 mL 2XYT (in 2-L flasks) supplemented with 0.5% (v/v) glycerol and necessary antibiotics. Production cultures were grown at 30° C., 250 rpm, until an OD$_{600}$ of 5 was reached. At this point, UDP-DATDH production was induced with the addition of 0.3 mM IPTG (final concentration), and cultures were grown at 30° C., 250 rpm, for 60 h. At t=0, 12 and 36 h post induction, 0.5% (v/v) glycerol was added to the production cultures. To maximize UDP-DATDH production, doses of 0.3% GlcNAc were supplied at t=0, 12, 24 and 36 h post induction. At the end of the duration of the experiment, cultures were harvested and the resulting cell pellets were analyzed by capillary-electrophoresis-MS.

Figure 8:
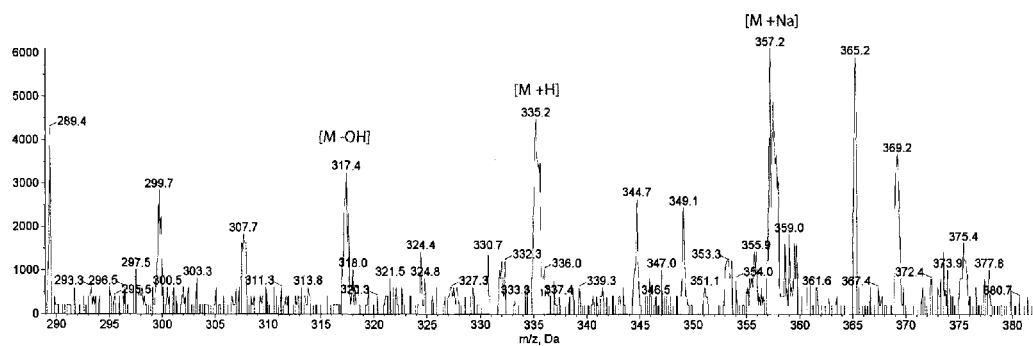
FIG. 8 shows an LCMS ESI+ spectrum demonstrating the effect of increasing intracellular acetyl-CoA levels on pseudaminic acid production. Acetyl-CoA synthesis was up-regulated through β-oxidation of palmitate, which was supplemented into the production culture at a total of 0.6 mg L-1. The LCMS ESI$^+$ analysis of cell-free culture broth from BRL04/pBRL175/pBRL178 cells (as described for FIG. 7) with the fermentation supplemented with palmitate clearly shows an ion-extraction peak for Pseudaminic acid with m/z values of 317 (M−OH), 335 (M+H) and 357 (M+Na).

To determine if the nanT⁻ nanA⁻ ΔnagA E. coli strain can at least generate the necessary UDP-linked DATDH sugar for pseudaminic and legionaminic acid production, the agm1/uap1 and pseBCH or pglFED genes were co-expressed in BRL04 as described. Analysis of clarified-cell lysates from production cultures of BRL04/pBRL178/pBRL151 with CE-MS in the negative-ion mode gave a distinct m/z peak at 630.9 (M−H) for UDP-6-deoxy-AltdiNAc (FIG. 8A). This peak was absent in the negative control (FIG. 8C). Similarly, the BRL04/pBRL178/pBRL152 strain was shown to produce UDP-BacdiNAc (FIG. 8B; m/z of 630.9). These results confirmed that the engineered E. coli strains are able to synthesize and produce UDP-linked 2,4-diacetmido-2,4,6-trideoxy hexoses.

The strain for production of UDP-BacdiNAc, BRL04/pBRL178/pBRL152, was deposited with the International Depositary Authority of Canada (National Microbiology Laboratory, Public Health Agency of Canada, 1015 Arlington Street, Winnipeg, Manitoba, Canada R3E 3R2) on Apr. 7, 2011, under deposit number 060411-01.

Example 6

Figure 9:
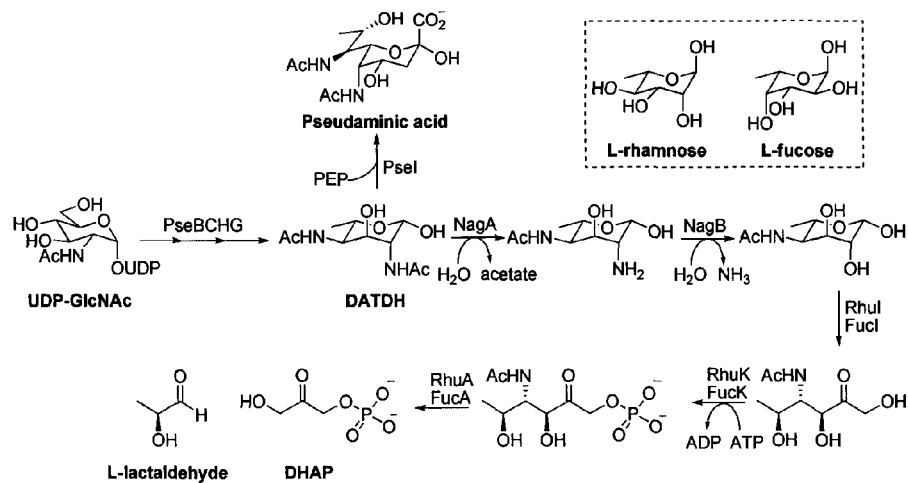
FIG. 9 shows the proposed catabolism for DATDHs in *E. coli*. Deacetylation of DATDH by NagA generates a 2-amino-6-deoxy intermediate that is likely deaminated through NagB catalysis. The resulting 4-acetamido-6-deoxy hexose is shunted into rhamnose and/or fucose metabolism with the final degradation products as dihydroxyacetone phosphate (DHAP) and lactaldehyde. Abbreviations: RhuI/FucI: isomerase, RhuK/FucK: kinase, RhuA/FucA: aldolase.

Construction of an *E. Coli* Strain Deficient in Enterobacterial Common Antigen (ECA), Colanic Acid, and Poly-N-Acetylglucosamine Biosynthesis There are no known biosynthetic or catabolic enzymes in *E. coli* involved in the metabolism of 2-acetamido-6-deoxy sugars (Keseler et al, 2009). However, the UDP-GlcNAc undecaprenyl-phosphate transferase, WecA (SEQ ID NO:18), from *E. coli* K-12 has been shown to accept UDP-linked 2,4-diacetamido-2,4,6-trideoxy hexoses (Linton et al, 2005). This evidence indicates that *E. coli* could salvage UDP-activated 2-acetamido-6-deoxy sugars by incorporating them into its own exo-polysaccharides; however, the substrate specificities of the glycosyltransferases in the majority of these pathways are poorly characterized (FIG. 9). To prevent unwanted glycosylation reactions that could consume UDP-linked Pse intermediates, the genes necessary for the biosynthesis of colanic acid (Stevenson et al, 1996), enterobacterial common antigen (ECA; Erbel et al, 2003), and poly-N-acetyl glucosamine (PGA; Itoh et al, 2008), and wecA were deleted from *E. coli* K-12 to test the effect on Pse production. It is worth noting that WecA may have the same effect on a strain for the production of legionaminic acid.

A wecA⁻ *E. coli* K-12 strain was obtained from the Keio Collection; this strain, BW25113 (Δ(araD-araB)567, ΔlacZ4787(::rrnB-3), lambda-, rph-1, Δ(rhaD-rhaB)568, hsdR514) (Table 6), has the wecA gene replaced with a kanamycin marker, and thus cannot biosynthesize ECA.

A λ(DE3) lysogen, encoding a T7 RNA polymerase under the control of a lac promoter, was inserted into the chromosome of the wecA⁻ *E. coli* K-12 strain, using the λ(DE3) lysogenization kit from Novagen (San Diego, Calif.), to generate the strain BRL11. Next, the entire colanic acid and poly-N-acetyglucosamine gene clusters were sequentially deleted from BRL11 using the lambda Red system. The plasmids pKD3, pCP20 and pKD46, were used for lambda Red recombination in *E. coli* (Lundgren, 2010). Primers used for the construction of the replacement, antibiotic-marker cassettes are given in Table 5.

Deletions were performed using standard molecular biology protocols. The colanic acid gene cluster region, wza-wcaM, was targeted first for deletion in the strain BRL11 and positive clones, were verified by kanamycin and chloramphenicol sensitivity. This markerless ΔwecA Δwza-wcaM *E. coli* strain was designated as BRL21.

The poly-N-acetylglucosamine gene cluster, pgaABCD (Rice et al, 2008), was then deleted from BRL21 to generate strain BRL25. The pgaABCD region was replaced with a chloramphenicol marker.

Expression of the PseBCHGI pathway in the biofilm deficient strain BRL25 did not yield any pseudaminic acid by proton NMR. The inability to detect Pse was attributed to a low conversion rate of UDP-GlcNAc into the desired pseudaminic acid product.

Example 7

Legionaminic Acid Production from *E. Coli*

Legionaminic acid is produced by co-expressing the pglFED (pBRL152) and agm1/uap1 (pBRL178) genes with the genes LegG and LegI (see Table 1) in *E. coli* BRL04. The LegG gene is derived from *Legionella pneumophila* (Glaze et al, 2008) (Lpg0753; SEQ ID NO:11) and the LegI gene is derived from *C. jejuni* (Schoenhofen et al, 2009) (Cj1327; SEQ ID NO:9) or *L. Pneumophila* (Glaze et al, 2008) (Lpg0752; SEQ ID NO:10).

Starter cultures are grown in 1 mL of LB media, supplemented with the necessary antibiotics, at 37° C., 200 rpm, for 18 h. A 20 mL F2 minimal media (in 250-mL shake-flask), supplemented with the necessary antibiotics, 0.25% casitone and 1% (v/v) glycerol is inoculated with 0.2 mL of starter culture. Production cultures are grown at 37° C., 200 rpm, until an $OD_{600}$ of 0.5 is reached. Legionaminic acid production is induced with 0.2 mM IPTG (final concentration), and the incubation temperature is lowered to 30° C. Production cultures are grown for 72 h and supplemented with 0.6% (v/v) glycerol at 0, 12 and 36 h post induction. At 0, 18 and 36 h post induction, doses of 0.2% GlcNAc are added for legionaminic acid biosynthesis/production.

Alternatively, pglFED (pBRL152) is co-expressed with agm1/uap1 (pBRL178) as just described above. To produce legionaminic acid, the expression is done in the presence of a UDP-BacdiNAc hydrolyzing 2-epimerase and a Leg synthase (Schoenhofen et al, 2009; Glaze et al, 2008). In yet

TABLE 5

Primers used for cassette construction. Primers (a1, a2) and (b1, b2) were used to PCR-amplify gene regions targeted for chromosomal deletion; primers (c1, c2) were used to generate the chloramphenicol-marker. The homology arms from (a1, a2) and (b1, b2) were fused with the marker from (c1, c2) to yield the full-length replacement cassette for lambda Red recombination.

| | | |
|---|---|---|
| colanic acid | a1-gttatcgatgatcaggttgcgc | SEQ ID NO: 37 |
| | a2-gaagcagctccagcctacaccgccagcttgctgcaggctttatag | SEQ ID NO: 38 |
| | b1-ctaaggaggatattcattgtttatttatcactttggcag | SEQ ID NO: 39 |
| | b2-gtaataacctcacattatccctg | SEQ ID NO: 40 |
| | c1-gtgtaggctggagctgcttc | SEQ ID NO: 41 |
| | c2-gtgtaggctggagctgcttc | SEQ ID NO: 42 |
| pgaDABC | a1-atgtattcaagtagcagaaaaaggtg | SEQ ID NO: 43 |
| | a2-gaagcagctccagcctacacggttattgctgagtgctgattttagtgc | SEQ ID NO: 44 |
| | b1-ctaaggaggatattcatgtctgggcgctgtacaataagctgcg | SEQ ID NO: 45 |
| | b2-ttatgcccggactagcgcttttttctgaaac | SEQ ID NO: 46 |
| | c1-gtgtaggctggagctgcttc | SEQ ID NO: 47 |
| | c2-atgggaattagccatggtcc | SEQ ID NO: 48 | another alternative, the UDP-BacdiNAc is recovered or partially recovered from the UDP-BacdiNAc culture of Example 5 and the UDP-BacdiNAc hydrolyzing 2-epimerase and Leg synthase enzymes are added to the recovered or partially recovered precursor.

Figure 2:
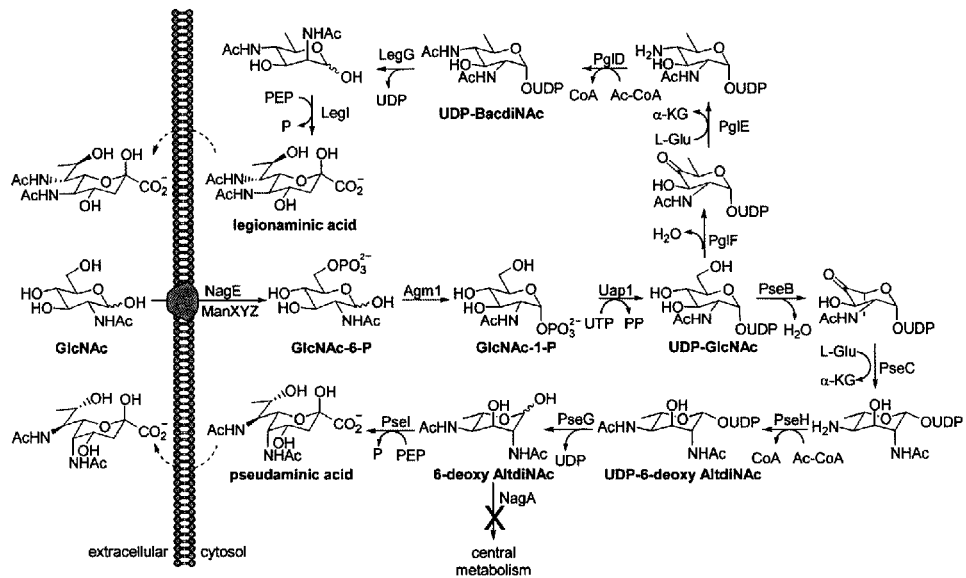
FIG. 2 shows the production pathway for pseudaminic acid, legionaminic acid, and UDP-activated 2,4-diacetamido-2,4,6-trideoxy hexoses (DATDH), specifically UDP-6-deoxy-AltdiNAc or UDP-BacdiNAc, by metabolically engineered *E. coli*. The non-native, yeast-derived enzymes, Agm1 and Uap1, were used to activate exogenously fed GlcNAc into UDP-GlcNAc. This substrate then entered either pseudaminic acid or legionaminic acid biosynthesis via PseBCHGI or PglFED/LegGI, respectively. Important for production was removal of the 2-acetamido deacetylase, NagA, which prevented the degradation of GlcNAc-6-P and possible degradation of 6-deoxy-AltdiNAc. Abbreviations: Agm1: N-acetylglucosamine mutase, Uap1: N-acetyl-glucosamine-1-P uridyltransferase, PseB/PglF: dehydratase, PseC/PglE: aminotransferase, PseH/PglD: acetyltransferase, PseG: UDP-sugar hydrolase, PseI: Pse synthase, LegG: UDP-sugar hydrolase and 2-epimerase, LegI: Leg synthase, NagA: GlcNAc-6-P deacetylase, NagE/ManXYZ; GlcNAc- and ManNAc-specific PTS transporters. See Table 1 for the PseBCHGI and PglFED/LegGI sugar products.
Figure 4:
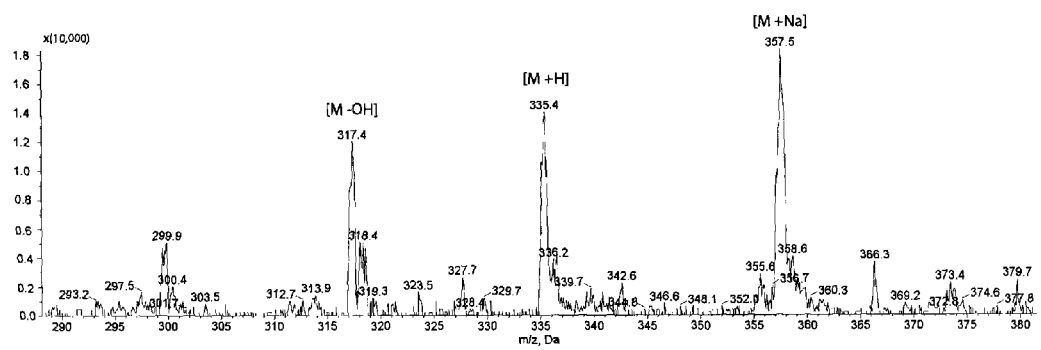
FIG. 4 shows LCMS ESI+ spectrum of pseudaminic acid in water, to validate the detection process (i.e. standard or positive control). Pseudaminic acid was separated by a Hypercarb HPLC column using an isocratic elution with water. Peaks at m/z of 317.4 (M−OH), 335.4 (M+H) and 357.5 (M+Na) were observed with a detection limit of 40 mg L$^{-1}$ of pseudaminic acid, where M is the characteristic mass of pseudaminic acid.
Figure 10:
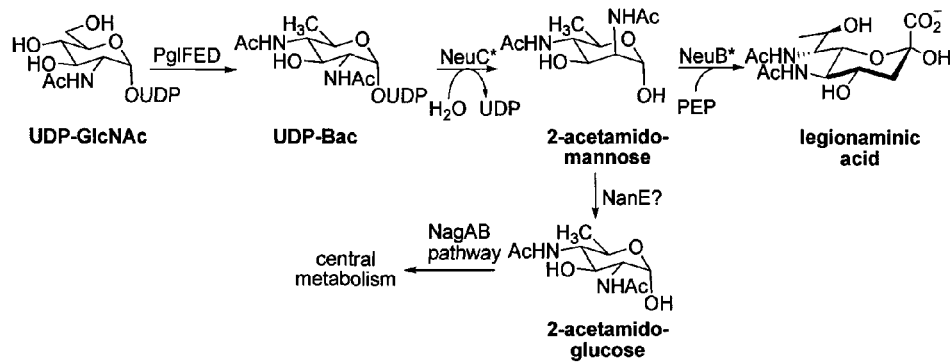
FIG. 10 shows the production of legionaminic acid from engineered *E. coli*. Legionaminic acid is biosynthesized from UDP-2,4-diacetamido-2,4,6-trideoxy-α-D-glucopyranose (UDP-BacdiNAc, labelled here as UDP-Bac) via a hydrolyzing 2-epimerase, LegG (or NeuC homolog), and a Leg synthase, LegI (or NeuB homolog). The epimerization at C2 by LegG generates a 2-acetamido-6-deoxy mannose intermediate (6-deoxy-MandiNAc) that is not likely accepted by the NagA/NagB catabolic pathway, but instead has to undergo a second epimerization at C2 via NanE to generate a degradable sugar adduct.

As shown in FIGS. 2 and 10, an epimerase hydrolyzes the glycosidic linkage of UDP-BacdiNAc and catalyzes an inversion of configuration at C2 to liberate 2,4-diacetamido-2,4,6-trideoxy-D-mannose. Unlike the pseudaminic acid DATDH-biosynthetic intermediate 6-deoxy-AltdiNAc, which has the glucose configuration at C2 (FIG. 2), the Leg-DATDH precursor 6-deoxy-MandiNAc is unlikely to be catabolized by NagA/NagB. Instead, its degradation could proceed through N-acetylmannose metabolism consisting of the ManNAc-6-P epimerase, NanE (SEQ ID NO:17) (Plumbridge & Vimr, 1999). NanE converts ManNAc-6-P into GlcNAc-6-P, and thus is required for catabolism of 2-acetamido mannose sugars in *E. coli*. Thus, a strain for production of legionaminic acid could also comprise an inactivated ManNAc-6-P epimerase gene.

Detection of Leg from production cultures may be done using a method similar to that described in Example 4.

Example 8

Summary of Plasmids and *E. Coli* Strains

The bacterial strains and plasmids used and prepared herein are described in Tables 6 and 7, respectively.

TABLE 6

*E. coli* strains used given with relevant genotypes. The BRL02 and BRL04 strains are derived from *E. coli* K-12 MG1655 (Kang et al, 2004). The BRL11, BRL21 and BRL25 strains are derived from *E. coli* BW25113. Resistance of strains to antibiotics kanamycin (Km), tetracycline (Tc) and/or chloramphenicol (Cm) is indicated.

| Strain | Relevant Genotype | Source | Marker |
| --- | --- | --- | --- |
| BL21(DE3) | F-, ompT, hsdSB(rB-, mB-), dcm, gal, λ(DE3) | Novagen | |
| BW25113 | Δ(araD-araB)567, ΔlacZ4787(::rrnB-3), lambda-, rph-1, Δ(rhaD-rhaB)568, hsdR514 | The Keio Collection | |
| BRL02 | nanT::Tn5(kan)-l-SceI nanA:tet λ(DE3) | WO2008/097366 | Km, Tc |
| BRL04 | BRL02 ΔnagA | WO2008/097366 | Km, Tc, |
| BRL11 | BW25113 wecA ::kan λ(DE3) | | Km |
| BRL21 | BW25113 ΔwecA Δwza-wcaM λ(DE3) | | |
| BRL25 | BW25113 ΔwecA Δwza-wcaM pgaABCD::cat λ(DE3) | | Cm |

TABLE 7

Plasmids constructed for the cloning and expression of the pseBCHGI and pglFED.

| Plasmid | Inserted Gene | Parental Vector | Antibiotic Marker | Origin of Inserted Gene |
| --- | --- | --- | --- | --- |
| pNRC8.1 | pseB | pCR-Blunt | $Km^R$ | PCR product |
| pNRC37.1 | pseC | pKH22 | $Am^R$ | Nde I/EcoR I glmU of pBRL35 |
| pNRC129.2 | pseH | pCR-Blunt | $Km^R$ | PCR product |
| pNRC133.1 | pseG | pBRL78 | $Km^R$ | Mutagenesis of pBRL78 |
| pNRC36.3 | pseI | pKH22 | $Am^R$ | Nhe I/EcoR I of pBRL79 |
| pBRL90 | pseB | pCR-Blunt | $Km^R$ | PCR product |
| pBRL91 | pseC | pCR-Blunt | $Km^R$ | PCR product |
| pBRL92 | pseH | pCR-Blunt | $Km^R$ | PCR product |
| pBRL94 | pseI | pCR-Blunt | $Km^R$ | PCR product |
| pBRL95 | pseB | pCR-Blunt | $Km^R$ | Mutagenesis of pBRL90 |
| pBRL97 | pseC | pKH22 | $Am^R$ | Nde I/EcoR I pseC of pBRL91 |
| pBRL98 | pseH | pKH22 | $Am^R$ | Nde I/EcoR I pseH of pBRL92 |
| pBRL99 | pseI | pKH22 | $Am^R$ | Nde I/EcoR I pseI of pBRL94 |
| pBRL100 | pseB | pKH22 | $Am^R$ | Nde I/EcoR I pseB of pBRL95 |
| pBRL143 | pglF | pKH22 | $Am^R$ | Nde I/EcoR I pglF of pBRL133 |
| pBRL144 | pglD | pKH22 | $Am^R$ | Nde I/EcoR I pglD of pBRL135 |
| pBRL145 | pglE | pKH22 | $Am^R$ | Nde I/EcoR I pglE of pBRL134 |
| pBRL146 | pseC | pBRL100 | $Am^R$ | Xba I/Avr II pseC of pBRL97 |
| pBRL149 | pglE | pBRL143 | $Am^R$ | Xba I/Avr II pglE of pBRL145 |
| pBRL151 | pseH | pBRL146 | $Am^R$ | Xba I/Avr II pseH of pBRL98 |
| pBRL152 | pglD | pBRL149 | $Am^R$ | Xba I/Avr II pglD of pBRL141 |
| pBRL171 | pseG | pCR-Blunt | $Km^R$ | PCR product |
| pBRL173 | pseG | pKH22 | $Am^R$ | Nde I/EcoR I pseG of pBRL171 |
| pBRL174 | pseG | pBRL151 | $Am^R$ | Xba I/Avr II pseG of pBRL173 |
| pBRL175 | pseI | pBRL174 | $Am^R$ | Xba I/Avr II pseI of pBRL99 |
| pBRL178 | agm1-uap1 | pKH61 | | |
| pBRL179 | agm1-uap1 | pBRL175 | | |

The embodiments and examples described herein are illustrative and are not meant to limit the scope of the invention as claimed. Variations of the foregoing embodiments, including alternatives, modifications and equivalents, are intended by the inventors to be encompassed by the claims. Furthermore, the discussed combination of features might not be necessary for the inventive solution.

REFERENCES

All patents, patent applications and publications referred to herein and throughout the application are hereby incorporated by reference in their entirety.

Chiba, Y., and Jigami, Y., 2007, Curr. Opin. Chem. Biol., 11: 670-676
Colombo, J. P.; Garcia-Rodenas, C.; Guesry, P. R.; Rey, J. Acta. Paediatr. Suppl. 2003, 92, 42-46.
Erbel, P. J. A.; Barr, K.; Gao, N.; Gerwig, G. J.; Rick, P. D.; Gardner, K. H. J. Bacteriol. 2003, 185, 1995-2004.
Glaze, P. A.; Watson, D. C.; Young, N. M.; Tanner, M. E. Biochemistry 2008, 47, 3272-3282.
Hayes, F. In E. coli Plasmid Vectors: Methods and Applications, Methods Molecular Biology 235; Humana Press: New Jersey, 2003; 1-17.
Higgins, E., 2010, Glycoconj. J., 27: 211-225
Hofmann, M.; Boles, E.; Zimmerman, F. K. Eur. J. Biochem. 1994, 221, 741-747.
Hsu, T. L.; Hanson, S. R.; Kishikawa, K.; Wang, S. K.; Sawa, M.; Wong, C. H. Proc. Natl. Acad. Sci. U.S.A. 2007, 104, 2614-2619.
Itoh, Y.; Rice, J. D.; Goller, C.; Pannuri, A.; Taylor, J.; Meisner, J.; Beveridge, T. J.; Preston, J. F.; Romeo, T. J. Bacteriol. 2008, 190, 3670-3680.
Jayant, S.; Khandare J. J.; Wang, Y.; Singh, A. P.; Vorsa, N.; Minko, T. Pharm. Res. 2007, 24, 2120-2130.
Keseler, I. M.; Bonavides-Martinez, C.; Collado-Vides, J.; Gama-Castro, S.; Gunsalus, R. P.; Johnson, D. A.; Krummenacker, M.; Nolan, L. M.; Paley, S.; Paulsen, I. T.; Peralta-Gil, M.; Santos-Zavaleta, A.; Shearer, A. G.; Karp, P. D. Nucleic Acid Res. 2009, 37, D464-D470.
Kiss, E.; Kereszt, A.; Barta, F.; Stephens, S.; Reuhs, B. L.; Kondorosi, A.; Putnoky, P. Mol. Plant. Microbe Interact. 2001, 14, 1395-1403.
Knirel, Y. A.; Shashkov, A. S.; Tsvetkov, Y. E.; Jansson, P. E.; Zahringer, U. Adv. Carbohydr. Chem. Biochem. 2003, 58, 371-417.
Lee, Y. J.;, Kubota, A.; Ishiwata, A.; Ito, Y. Tetrahedron Lett. 2010, 52, 418.
Lewis, A. L.; Desa, N.; Hansen, E. E.; Knirel, Y. A.; Gordon, J. I.; Gagneux, P.; Nizet, V.; Varki, A. Proc. Natl. Acad. Sci. U.S.A. 2009, 106, 13552-13557.
Lin et al., 2006, Appl. Microbiol. Biotechnol., 71: 870-874
Linton, D.; Dorrell, N.; Hitchen, P. G.; Amber, S.; Karlyshev, A. V.; Morris, H. R.; Dell, A.; Valvano, M. A.; Aebi, M.; Wren, B. W. Mol. Microbiol. 2005, 55, 1695-1703.
Lundgren B. R. and Christopher N. Boddy Sialic acid and N-acyl sialic acid analog production by fermentation of metabolically and genetically engineered Escherichia coli Org. Biomol. Chem., 2007, 5, 1903-1909
Lundgren, B. R. (2010). Metabolically and genetically engineering Escherichia coli for the production of sialic acid and sialic acid analogs. Doctoral dissertation, Syracuse University, Syracuse, N.Y., USA
Mahal, L. K.; Yarema K. J.; Bertozzi, C. R. Science 1997, 276, 11251128.
Manzi, A. E.; Diaz, S.; Varki, A. Anal. Biochem. 1990, 188, 20-32.
McNally, D. J.; Aubry, A. J.; Hui, J. P. M.; Khieu, N. H.; Whitfield, D.; Ewing, C. P.; Guerry, P.; Brisson, J. R.; Logan, S. M.; Soo, E. C. J. Biol. Chem. 2007, 282, 14463-14475.
Mio, T.; Yabe, T.; Arisawa, M.; Yamada-Okabe, H. J. Biol. Chem. 1998, 273, 14392-14397.
Oliver, N. B.; Chen, M. M.; Behr, J. R.; Imperiali, B. Biochemistry 2006, 45, 13659-13669.
Plumbridge, J. A.; Cochet, O.; Souza, J. M.; Altamirano, M. M.; Calcagno, M. L.; Badet, B. J. Bacteriol. 1993, 175, 4951-4956.
Plumbridge, J.; Vimr, E. J. Bacteriol. 1999, 181, 47-54.
Rice J. D., Carlos Goller, Archana Pannuri, Jeannette Taylor, Jeffrey Meisner, Terry J. Beveridge, James F. Preston III, and Tony Romeo (2008), Roles of pgaABCD Genes in Synthesis, Modification, and Export of the Escherichia coli Biofilm Adhesin Poly-β-1,6-N-Acetyl-D-Glucosamine Journal of Bacteriology, 190, 3670-3680.
Schoenhofen, I. C.; McNally, D. J.; Brisson, J.; Logan, S. M. Glycobiology 2006a, 16, 8C-14C.
Schoenhofen, I. C.; McNally, D. J.; Vinogradov, E.; Whitfield, D.; Young, N. M.; Dick, S.; Wakarchuk, W. W.; Brisson, J.; Logan, S. M. J. Biol. Chem. 2006b, 281, 723-732.
Schoenhofen, I. C.; Vinogradov, E.; Whitfield, D.; Brisson, J.; Logan, S. M. Glycobiology 2009, 19, 715-725.
Sethuraman, N., and Stadheim, T. A. 2006, Curr. Opin. Biotechnol., 17: 341-346
Studier, F. W.; Rosenberg, A. H.; Dunn, J. J.; Dubendorff, J. W. Methods Enzymol. 1990, 185, 60-89.
Tsvetkov, Y. E., Shashkov, A. S., Knirel, Y. A., and Zahringer, U., 2001, Carbohydrate Research, 335:221-243.
von Itzstein, M. Nat. Rev. Drug Discovery 2007, 6, 967-974.
Wang, B.; Yu, B.; Karim, M.; Hu, H.; Sun, Y.; McGreevy, P.; Petocz, P.; Held, S.; Brand-Miller, J. Am. J. Clin. Nutr. 2007, 85, 561-569.
Y. Kang, T. Durfee, J. D. Glasner, Y. Qiu, D. Frisch, K. M. Winterberg, and F. R. Blattner (2004). "Systematic mutagenesis of the Escherichia coli genome." J Bacteriol 186: 4921-30.
WO 2008/097366

The invention claimed is:

1. A recombinant cell for the production of pseudaminic acid, comprising an inactivated GlcNAc-6-P deacetylase gene, a gene encoding PseB enzyme function, a gene encoding PseC enzyme function, a gene encoding PseH enzyme function, a gene encoding PseI enzyme function, a gene encoding PseG enzyme function, a gene encoding a GlcNAc-6-P mutase, and a gene encoding a GlcNAc-1-P uridyltransferase.

2. The recombinant cell of claim 1, further comprising at least one of an inactivated nanT sialic acid transporter gene, an inactivated nanA sialic acid aldolase gene or a gene encoding an acetyl-CoA synthase.

3. The recombinant cell of claim 1, wherein the recombinant cell is an *E. coli* cell and comprises an inactivated nanT sialic acid transporter gene, an inactivated nanA sialic acid aldolase gene, an inactivated nagA GlcNAc-6-P deacetylase gene, a PseB gene encoding SEQ ID NO:1, a PseC gene encoding SEQ ID NO:2, a PseH gene encoding SEQ ID NO:3, a PseI gene encoding SEQ ID NO:4, a PseG gene encoding SEQ ID NO:5, the agm1 GlcNAc-6-P mutase gene, and the uap1 GlcNAc-1-P uridyltransferase gene.

4. The recombinant cell for the production of pseudaminic acid of claim 1, wherein the cell is that of IDAC deposit No. 060411-02.

5. A method for the production of pseudaminic acid, comprising growing the recombinant cell of claim 1 and recovering the produced pseudaminic acid.

6. The method of claim 5, wherein growth medium for the recombinant cell is supplemented with palmitate.

7. A recombinant cell for the production of UDP-2,4-diacetamido-2,4,6-trideoxy-β-L-altropyranose (UDP-6-deoxy-AltdiNAc), comprising an inactivated GlcNAc-6-P deacetylase gene, a gene encoding PseB enzyme function, a gene encoding PseC enzyme function, a gene encoding PseH enzyme function, a gene encoding GlcNAc-6-P mutase, and a gene encoding a GlcNAc-1-P uridyltransferase.

8. The recombinant cell of claim 7, further comprising at least one of an inactivated nanT sialic acid transporter gene, an inactivated nanA sialic acid aldolase gene or a gene encoding acetyl-CoA synthase.

9. The recombinant cell of claim 7, wherein the recombinant cell is an *E. coli* cell and comprises an inactivated nanT sialic acid transporter gene, an inactivated nanA sialic acid aldolase gene, an inactivated nagA GlcNAc-6-P deacetylase gene, a PseB gene encoding SEQ ID NO:1, a PseC gene encoding SEQ ID NO:2, a PseH gene encoding SEQ ID NO:3, the agm1GlcNAc-6-P mutase gene, and the uap1GlcNAc-1-P uridyltransferase gene.

10. A method for the production of UDP-2,4-diacetamido-2,4,6-trideoxy-β-L-altropyranose (UDP-6-deoxy-AltdiNAc), comprising growing the recombinant cell of claim 7 and recovering the produced UDP-6-deoxy-AltdiNAc.

11. The method of claim 10, wherein growth medium for the recombinant cell is supplemented with palmitate.

\* \* \* \* \*

SEQUENCE LISTING

<160> NUMBER OF SEQ ID NOS: 48

<210> SEQ ID NO 1
<211> LENGTH: 333
<212> TYPE: PRT
<213> ORGANISM: H. pylori

<400> SEQUENCE: 1

Met Pro Asn His Gln Asn Met Leu Asp Asn Gln Thr Ile Leu Ile Thr
1               5                   10                  15

Gly Gly Thr Gly Ser Phe Gly Lys Cys Phe Val Arg Lys Val Leu Asp
                20                  25                  30

Thr Thr Asn Ala Lys Lys Ile Ile Val Tyr Ser Arg Asp Glu Leu Lys
            35                  40                  45

Gln Ser Glu Met Ala Met Glu Phe Asn Asp Pro Arg Met Arg Phe Phe
        50                  55                  60

Ile Gly Asp Val Arg Asp Leu Glu Arg Leu Asn Tyr Ala Leu Glu Gly
65                  70                  75                  80

Val Asp Ile Cys Ile His Ala Ala Leu Lys His Val Pro Ile Ala
                85                  90                  95

Glu Tyr Asn Pro Leu Glu Cys Ile Lys Thr Asn Ile Met Gly Ala Ser
                100                 105                 110

Asn Val Ile Asn Ala Cys Leu Lys Asn Ala Ile Ser Gln Val Ile Ala
            115                 120                 125

Leu Ser Thr Asp Lys Ala Ala Asn Pro Ile Asn Leu Tyr Gly Ala Thr
        130                 135                 140

Lys Leu Cys Ser Asp Lys Leu Phe Val Ser Ala Asn Asn Phe Lys Gly
145                 150                 155                 160

Ser Ser Gln Thr Gln Phe Ser Val Val Arg Tyr Gly Asn Val Val Gly
                165                 170                 175

Ser Arg Gly Ser Val Val Pro Phe Phe Lys Lys Leu Val Gln Asn Lys
                180                 185                 190

Ala Ser Glu Ile Pro Ile Thr Asp Ile Arg Met Thr Arg Phe Trp Ile
            195                 200                 205

Thr Leu Asp Glu Gly Val Ser Phe Val Leu Lys Ser Leu Lys Arg Met
        210                 215                 220

His Gly Gly Glu Ile Phe Val Pro Lys Ile Pro Ser Met Lys Met Thr
225                 230                 235                 240

Asp Leu Ala Lys Ala Leu Ala Pro Asn Thr Pro Thr Lys Ile Ile Gly
                245                 250                 255

Ile Arg Pro Gly Glu Lys Leu His Glu Val Met Ile Pro Lys Asp Glu
                260                 265                 270

Ser His Leu Ala Leu Glu Phe Glu Asp Phe Ile Ile Gln Pro Thr
            275                 280                 285

Ile Ser Phe Gln Thr Pro Lys Asp Tyr Thr Leu Thr Lys Leu His Glu
        290                 295                 300

Lys Gly Gln Lys Val Ala Pro Asp Phe Glu Tyr Ser Ser His Asn Asn
305                 310                 315                 320

Asn Gln Trp Leu Glu Pro Asp Leu Leu Lys Leu Leu
                325                 330

<210> SEQ ID NO 2
<211> LENGTH: 375
<212> TYPE: PRT
<213> ORGANISM: H. pylori

<400> SEQUENCE: 2

Met Lys Glu Phe Ala Tyr Ser Glu Pro Cys Leu Asp Lys Glu Asp Lys
1               5                   10                  15

Lys Ala Val Leu Glu Val Leu Asn Ser Lys Gln Leu Thr Gln Gly Lys
                20                  25                  30

-continued

Arg Ser Leu Leu Phe Glu Glu Ala Leu Cys Glu Phe Leu Gly Val Lys
         35                  40                  45

His Ala Leu Val Phe Asn Ser Ala Thr Ser Ala Leu Leu Thr Leu Tyr
 50                  55                  60

Arg Asn Phe Ser Glu Phe Ser Ala Asp Arg Asn Glu Ile Ile Thr Thr
 65                  70                  75                  80

Pro Ile Ser Phe Val Ala Thr Ala Asn Met Leu Leu Glu Ser Gly Tyr
                 85                  90                  95

Thr Pro Val Phe Ala Gly Ile Lys Asn Asp Gly Asn Ile Asp Glu Leu
                100                 105                 110

Ala Leu Glu Lys Leu Ile Asn Glu Arg Thr Lys Ala Ile Val Ser Val
            115                 120                 125

Asp Tyr Ala Gly Lys Ser Val Glu Val Glu Ser Val Gln Lys Leu Cys
130                 135                 140

Lys Lys His Ser Leu Ser Phe Leu Ser Asp Ser Ser His Ala Leu Gly
145                 150                 155                 160

Ser Glu Tyr Gln Asn Lys Lys Val Gly Gly Phe Ala Leu Ala Ser Val
                165                 170                 175

Phe Ser Phe His Ala Ile Lys Pro Ile Thr Thr Ala Glu Gly Gly Ala
                180                 185                 190

Val Val Thr Asn Asp Ser Glu Leu His Glu Lys Met Lys Leu Phe Arg
            195                 200                 205

Ser His Gly Met Leu Lys Lys Asp Phe Glu Gly Glu Val Lys Ser
210                 215                 220

Ile Gly His Asn Phe Arg Leu Asn Glu Ile Gln Ser Ala Leu Gly Leu
225                 230                 235                 240

Ser Gln Leu Lys Lys Ala Pro Phe Leu Met Gln Lys Arg Glu Glu Ala
                245                 250                 255

Ala Leu Thr Tyr Asp Arg Ile Phe Lys Asp Asn Pro Tyr Phe Thr Pro
                260                 265                 270

Leu His Pro Leu Leu Lys Asp Lys Ser Ser Asn His Leu Tyr Pro Ile
            275                 280                 285

Leu Met His Gln Lys Phe Phe Thr Cys Lys Lys Leu Ile Leu Glu Ser
290                 295                 300

Leu His Lys Arg Gly Ile Leu Ala Gln Val His Tyr Lys Pro Ile Tyr
305                 310                 315                 320

Gln Tyr Gln Leu Tyr Gln Gln Leu Phe Asn Thr Ala Pro Leu Lys Ser
                325                 330                 335

Ala Glu Asp Phe Tyr His Ala Glu Ile Ser Leu Pro Cys His Ala Asn
                340                 345                 350

Leu Asn Leu Glu Ser Val Gln Asn Ile Ala His Ser Val Leu Lys Thr
            355                 360                 365

Phe Glu Ser Phe Lys Ile Glu
370                 375

<210> SEQ ID NO 3
<211> LENGTH: 180
<212> TYPE: PRT
<213> ORGANISM: H. pylori

<400> SEQUENCE: 3

Met Lys Lys Asn Tyr Ser Tyr Lys Asn Ile Gln Ala Ile Asp Phe Thr
1               5                   10                  15

Asn Leu Asn Asp Gly Glu Lys Leu Leu Val Leu Glu Phe Arg Asn His
            20                  25                  30

```
Pro Asn Thr Ala Leu Trp Met Tyr Ser Thr Phe Ile Ser Leu Lys Thr
             35                  40                  45

His Leu Gln Phe Ile Glu Asp Leu Lys Asn Ser Pro Asn His Arg Tyr
 50                  55                  60

Phe Leu Phe Lys Glu Glu Gly Val Tyr Leu Gly Val Gly Ser Ile Thr
 65                  70                  75                  80

Lys Ile Asn Phe Phe His Lys His Gly Tyr Leu Gly Ile Tyr Lys Asn
                     85                  90                  95

Pro Phe Leu Lys Asn Gly Gly Glu Thr Ile Leu Lys Ala Leu Glu Phe
                 100                 105                 110

Ile Ala Phe Glu Glu Phe Gln Leu His Ser Leu His Leu Gly Val Met
             115                 120                 125

Glu Asn Asn Phe Lys Ala Ile Ala Phe Tyr Glu Lys Asn His Tyr Glu
 130                 135                 140

Leu Glu Gly Arg Leu Lys Gly Phe Ile Ser Lys Asp Lys Glu Phe Ile
145                 150                 155                 160

Asp Val Leu Leu Tyr Tyr Lys Asp Lys Gly Tyr Asn Asp Gln Ser
                 165                 170                 175

Leu Leu Lys Leu
         180

<210> SEQ ID NO 4
<211> LENGTH: 340
<212> TYPE: PRT
<213> ORGANISM: H. pylori

<400> SEQUENCE: 4

Met Leu Gln Pro Pro Lys Ile Val Ala Glu Leu Ser Ala Asn His Asn
  1               5                  10                  15

Gln Asp Leu Asn Leu Ala Lys Glu Ser Leu His Ala Ile Lys Glu Ser
             20                  25                  30

Gly Ala Asp Phe Val Lys Leu Gln Thr Tyr Thr Pro Ser Cys Met Thr
             35                  40                  45

Leu Asn Ser Lys Glu Asp Pro Phe Ile Ile Gln Gly Thr Leu Trp Asp
 50                  55                  60

Lys Glu Asn Leu Tyr Glu Leu Tyr Gln Lys Ala Ser Thr Pro Leu Glu
 65                  70                  75                  80

Trp His Ala Glu Leu Phe Glu Leu Ala Arg Lys Leu Asp Leu Gly Ile
                 85                  90                  95

Phe Ser Ser Pro Phe Ser Ser Gln Ala Leu Glu Leu Leu Glu Ser Leu
             100                 105                 110

Asn Cys Pro Met Tyr Lys Ile Ala Ser Phe Glu Ile Val Asp Leu Asp
             115                 120                 125

Leu Ile Glu Lys Ala Ala Arg Thr Gln Lys Pro Ile Ile Leu Ser Ser
130                 135                 140

Gly Ile Ala Thr His Thr Glu Leu Gln Asp Ala Ile Ser Leu Cys Arg
145                 150                 155                 160

Arg Val Asn Asn Phe Asp Ile Thr Leu Leu Lys Cys Val Ser Ala Tyr
                 165                 170                 175

Pro Ser Lys Ile Glu Asp Ala Asn Leu Leu Ser Met Val Lys Leu Gly
             180                 185                 190

Glu Ile Phe Gly Val Lys Phe Gly Leu Ser Asp His Thr Ile Gly Ser
             195                 200                 205

Leu Cys Pro Ile Leu Ala Thr Thr Leu Gly Ala Ser Met Ile Glu Lys
210                 215                 220
```

```
His Phe Ile Leu Asn Lys Ser Leu Gln Thr Pro Asp Ser Ala Phe Ser
225                 230                 235                 240

Met Asp Phe Asn Gly Phe Lys Ser Met Val Glu Ala Ile Lys Gln Ser
            245                 250                 255

Val Leu Ala Leu Gly Glu Glu Pro Arg Ile Asn Pro Lys Thr Leu
        260                 265                 270

Glu Lys Arg Arg Phe Phe Ala Arg Ser Leu Phe Val Ile Lys Asp Ile
        275                 280                 285

Gln Lys Gly Glu Ala Leu Thr Glu Asn Asn Ile Lys Ala Leu Arg Pro
        290                 295                 300

Asn Leu Gly Leu His Pro Lys Phe Tyr Lys Glu Ile Leu Gly Gln Lys
305                 310                 315                 320

Ala Ser Lys Phe Leu Lys Ala Asn Thr Pro Leu Ser Ala Asp Asp Ile
            325                 330                 335

Glu Arg Ser Leu
            340

<210> SEQ ID NO 5
<211> LENGTH: 274
<212> TYPE: PRT
<213> ORGANISM: C. jejuni

<400> SEQUENCE: 5

Met Lys Val Leu Phe Arg Ser Asp Ser Ser Gln Ile Gly Phe Gly
1               5                   10                  15

His Ile Lys Arg Asp Leu Val Leu Ala Lys Gln Tyr Ser Asp Val Ser
            20                  25                  30

Phe Ala Cys Leu Pro Leu Glu Gly Ser Leu Ile Asp Glu Ile Pro Tyr
        35                  40                  45

Pro Val Tyr Glu Leu Ser Ser Gly Ser Ile Tyr Glu Leu Ile Asn Leu
    50                  55                  60

Ile Lys Glu Glu Lys Phe Glu Leu Leu Ile Ile Asp His Tyr Gly Ile
65                  70                  75                  80

Ser Val Asp Asp Glu Lys Leu Ile Lys Leu Glu Thr Gly Val Lys Ile
                85                  90                  95

Leu Ser Phe Asp Asp Glu Ile Lys Pro His His Cys Asp Ile Leu Leu
            100                 105                 110

Asn Val Asn Ala Tyr Ala Lys Ala Ser Asp Tyr Glu Gly Leu Val Pro
        115                 120                 125

Phe Lys Cys Glu Val Arg Cys Gly Phe Ser Tyr Ala Leu Ile Arg Glu
    130                 135                 140

Glu Phe Tyr Gln Glu Ala Lys Glu Asn Arg Glu Lys Lys Tyr Asp Phe
145                 150                 155                 160

Phe Ile Cys Met Gly Gly Thr Asp Ile Lys Asn Leu Ser Leu Gln Ile
                165                 170                 175

Ala Ser Glu Leu Pro Lys Thr Lys Ile Ile Ser Ile Ala Thr Ser Ser
            180                 185                 190

Ser Asn Pro Asn Leu Lys Lys Leu Gln Lys Phe Ala Lys Leu His Asn
        195                 200                 205

Asn Ile Arg Leu Phe Ile Asp His Glu Asn Ile Ala Lys Leu Met Asn
    210                 215                 220

Glu Ser Asn Lys Leu Ile Ile Ser Ala Ser Ser Leu Val Asn Glu Ala
225                 230                 235                 240

Leu Leu Leu Lys Ala Asn Phe Lys Ala Ile Cys Tyr Val Lys Asn Gln
                245                 250                 255
```

```
Glu Ser Thr Ala Thr Trp Leu Ala Lys Lys Gly Tyr Glu Val Glu Tyr
            260                 265                 270
Lys Tyr
```

<210> SEQ ID NO 6
<211> LENGTH: 590
<212> TYPE: PRT
<213> ORGANISM: C. jejuni

<400> SEQUENCE: 6

```
Met Ile Phe Tyr Lys Ser Lys Arg Leu Ala Phe Phe Leu Thr Ser Asp
1               5                   10                  15

Ile Val Leu Ile Leu Leu Ser Val Tyr Leu Ala Phe Ser Leu Arg Phe
            20                  25                  30

Ser Gly Asp Ile Pro Ser Ile Phe Tyr His Gly Met Met Val Ser Ala
            35                  40                  45

Ile Ile Leu Leu Val Leu Lys Leu Ser Phe Leu Phe Val Phe Arg Ile
        50                  55                  60

Tyr Lys Val Ala Trp Arg Phe Phe Ser Leu Asn Glu Ala Arg Lys Ile
65                  70                  75                  80

Phe Ile Ala Leu Leu Leu Ala Glu Phe Cys Phe Phe Leu Ile Phe Tyr
                85                  90                  95

Phe Phe Ser Asp Phe Phe Asn Pro Phe Pro Arg Ser Ala Ile Val Ile
            100                 105                 110

Asp Phe Val Leu Ser Tyr Met Phe Ile Gly Thr Leu Arg Ile Ser Lys
            115                 120                 125

Arg Met Leu Val Asp Phe Lys Pro Ser Arg Met Lys Glu Glu Glu Thr
130                 135                 140

Pro Cys Ile Val Val Gly Ala Thr Ser Lys Ala Leu His Leu Leu Lys
145                 150                 155                 160

Gly Ala Lys Glu Gly Ser Leu Gly Leu Phe Pro Val Gly Val Val Asp
                165                 170                 175

Ala Arg Lys Glu Leu Ile Gly Thr Tyr Cys Asp Lys Phe Ile Val Glu
            180                 185                 190

Glu Lys Glu Lys Ile Lys Ser Tyr Val Glu Gln Gly Val Lys Thr Ala
            195                 200                 205

Ile Ile Ala Leu Arg Leu Glu Gln Glu Glu Leu Lys Lys Leu Phe Glu
        210                 215                 220

Glu Leu Val Ala Tyr Gly Ile Cys Asp Val Lys Ile Phe Ser Phe Thr
225                 230                 235                 240

Arg Asn Glu Ala Arg Asp Ile Ser Ile Glu Asp Leu Leu Ala Arg Lys
                245                 250                 255

Pro Lys Asp Leu Asp Asp Ser Ala Val Ala Ala Phe Leu Lys Asp Lys
            260                 265                 270

Val Val Leu Val Ser Gly Ala Gly Gly Thr Ile Gly Ser Glu Leu Cys
            275                 280                 285

Lys Gln Cys Ile Lys Phe Gly Ala Lys His Leu Ile Met Val Asp His
        290                 295                 300

Ser Glu Tyr Asn Leu Tyr Lys Ile Asn Asp Asp Leu Asn Leu Tyr Lys
305                 310                 315                 320

Glu Lys Ile Thr Pro Ile Leu Leu Ser Ile Leu Asp Lys Gln Ser Leu
                325                 330                 335

Asp Glu Val Leu Lys Thr Tyr Lys Pro Glu Leu Ile Leu His Ala Ala
            340                 345                 350
```

```
Ala Tyr Lys His Val Pro Leu Cys Glu Gln Asn Pro His Ser Ala Val
            355                 360                 365

Ile Asn Asn Ile Leu Gly Thr Lys Ile Leu Cys Asp Ser Ala Lys Glu
        370                 375                 380

Asn Lys Val Ala Lys Phe Val Met Ile Ser Thr Asp Lys Ala Val Arg
385                 390                 395                 400

Pro Thr Asn Ile Met Gly Cys Thr Lys Arg Val Cys Glu Leu Tyr Thr
                405                 410                 415

Leu Ser Met Ser Asp Glu Asn Phe Glu Val Ala Cys Val Arg Phe Gly
            420                 425                 430

Asn Val Leu Gly Ser Ser Gly Ser Val Ile Pro Lys Phe Lys Ala Gln
            435                 440                 445

Ile Ala Asn Asn Glu Pro Leu Thr Leu Thr His Pro Asp Ile Val Arg
        450                 455                 460

Tyr Phe Met Leu Val Ala Glu Ala Val Gln Leu Val Leu Gln Ala Gly
465                 470                 475                 480

Ala Ile Ala Lys Gly Gly Glu Leu Phe Val Leu Asp Met Gly Lys Pro
                485                 490                 495

Val Lys Ile Ile Asp Leu Ala Lys Lys Met Leu Leu Leu Ser Asn Arg
            500                 505                 510

Asn Asp Leu Glu Ile Lys Ile Thr Gly Leu Arg Lys Gly Glu Lys Leu
        515                 520                 525

Tyr Glu Glu Leu Leu Ile Asp Glu Asn Asp Ala Lys Thr Gln Tyr Glu
            530                 535                 540

Ser Ile Phe Val Ala Lys Asn Glu Lys Val Asp Leu Asp Trp Leu Asn
545                 550                 555                 560

Lys Glu Ile Glu Asn Leu Gln Ile Cys Glu Asp Ile Ser Glu Ala Leu
                565                 570                 575

Leu Lys Ile Val Pro Glu Phe Lys His Asn Lys Glu Gly Val
            580                 585                 590

<210> SEQ ID NO 7
<211> LENGTH: 386
<212> TYPE: PRT
<213> ORGANISM: C. jejuni

<400> SEQUENCE: 7

Met Arg Phe Phe Leu Ser Pro Pro His Met Gly Gly Asn Glu Leu Lys
1               5                   10                  15

Tyr Ile Glu Glu Val Phe Lys Ser Asn Tyr Ile Ala Pro Leu Gly Glu
            20                  25                  30

Phe Val Asn Arg Phe Glu Gln Ser Val Lys Ala Tyr Ser Lys Ser Glu
        35                  40                  45

Asn Ala Leu Ala Leu Asn Ser Ala Thr Ala Ala Leu His Leu Ala Leu
    50                  55                  60

Arg Val Ala Gly Val Lys Gln Asp Asp Ile Val Leu Ala Ser Ser Phe
65                  70                  75                  80

Thr Phe Ile Ala Ser Val Ala Pro Ile Cys Tyr Leu Lys Ala Lys Pro
                85                  90                  95

Val Phe Ile Asp Cys Asp Glu Thr Tyr Asn Ile Asp Val Asp Leu Leu
            100                 105                 110

Lys Leu Ala Ile Lys Glu Cys Glu Lys Lys Pro Lys Ala Leu Ile Leu
        115                 120                 125

Thr His Leu Tyr Gly Asn Ala Ala Lys Met Asp Glu Ile Val Glu Ile
    130                 135                 140
```

Cys Lys Glu Asn Glu Ile Val Leu Ile Glu Asp Ala Ala Glu Ala Leu
145                 150                 155                 160

Gly Ser Phe Tyr Lys Asn Lys Ala Leu Gly Thr Phe Gly Glu Phe Gly
                165                 170                 175

Ala Tyr Ser Tyr Asn Gly Asn Lys Ile Ile Thr Thr Ser Gly Gly Gly
                180                 185                 190

Met Leu Ile Gly Lys Asn Lys Glu Lys Ile Glu Lys Ala Arg Phe Tyr
            195                 200                 205

Ser Thr Gln Ala Arg Glu Asn Cys Leu His Tyr Glu His Leu Asp Tyr
            210                 215                 220

Gly Tyr Asn Tyr Arg Leu Ser Asn Val Leu Gly Ala Ile Gly Val Ala
225                 230                 235                 240

Gln Met Glu Val Leu Glu Gln Arg Val Leu Lys Lys Arg Glu Ile Tyr
                245                 250                 255

Glu Trp Tyr Lys Glu Phe Leu Gly Glu Cys Phe Ser Phe Leu Asp Glu
                260                 265                 270

Leu Glu Asn Ser Arg Ser Asn Arg Trp Leu Ser Thr Ala Leu Ile Asp
            275                 280                 285

Phe Asp Lys Asn Glu Leu Asn Ser Cys Gln Lys Asp Ile Asn Ile Ser
290                 295                 300

Gln Lys Asn Ile Thr Leu His Pro Lys Ile Ser Lys Leu Ile Glu Asp
305                 310                 315                 320

Leu Lys Asn Glu Gln Ile Glu Thr Arg Pro Leu Trp Lys Ala Met His
                325                 330                 335

Ala Gln Glu Val Phe Lys Gly Ala Lys Ala Tyr Leu Asn Gly Asn Ser
                340                 345                 350

Glu Leu Phe Phe Gln Lys Gly Ile Cys Leu Pro Ser Gly Thr Ala Met
            355                 360                 365

Ser Lys Asp Asp Val Tyr Glu Ile Ser Lys Leu Ile Leu Lys Ser Ile
            370                 375                 380

Lys Ala
385

<210> SEQ ID NO 8
<211> LENGTH: 195
<212> TYPE: PRT
<213> ORGANISM: C. jejuni

<400> SEQUENCE: 8

Met Ala Arg Thr Glu Lys Ile Tyr Ile Tyr Gly Ala Ser Gly His Gly
1               5                   10                  15

Leu Val Cys Glu Asp Val Ala Lys Asn Met Gly Tyr Lys Glu Cys Ile
                20                  25                  30

Phe Leu Asp Asp Phe Lys Gly Met Lys Phe Glu Ser Thr Leu Pro Lys
            35                  40                  45

Tyr Asp Phe Phe Ile Ala Ile Gly Asn Asn Glu Ile Arg Lys Lys Ile
        50                  55                  60

Tyr Gln Lys Ile Ser Glu Asn Gly Phe Lys Ile Val Asn Leu Ile His
65                  70                  75                  80

Lys Ser Ala Leu Ile Ser Pro Ser Ala Ile Val Glu Glu Asn Ala Gly
                85                  90                  95

Ile Leu Ile Met Pro Tyr Val Val Ile Asn Ala Lys Ala Lys Ile Glu
            100                 105                 110

Lys Gly Val Ile Leu Asn Thr Ser Ser Val Ile Glu His Glu Cys Val

```
                     115                 120                 125
Ile Gly Glu Phe Ser His Val Ser Val Gly Ala Lys Cys Ala Gly Asn
    130                 135                 140

Val Lys Ile Gly Lys Asn Cys Phe Leu Gly Ile Asn Ser Cys Val Leu
145                 150                 155                 160

Pro Asn Leu Ser Leu Ala Asp Asp Ser Ile Leu Gly Gly Gly Ala Thr
                165                 170                 175

Leu Val Lys Asn Gln Asp Glu Lys Gly Val Phe Val Gly Val Pro Ala
            180                 185                 190

Lys Arg Met
        195

<210> SEQ ID NO 9
<211> LENGTH: 334
<212> TYPE: PRT
<213> ORGANISM: C. jejuni

<400> SEQUENCE: 9

Met Lys Lys Thr Leu Ile Ile Ala Glu Ala Gly Val Asn His Asn Gly
1               5                   10                  15

Asp Leu Asn Leu Ala Lys Lys Leu Ile Glu Ile Ala Ala Asp Ser Gly
            20                  25                  30

Ala Asp Phe Val Lys Phe Gln Ser Phe Lys Ala Lys Asn Cys Ile Ser
        35                  40                  45

Thr Lys Ala Lys Lys Ala Pro Tyr Gln Leu Lys Thr Thr Ala Asn Asp
    50                  55                  60

Glu Ser Gln Leu Gln Met Val Gln Lys Leu Glu Leu Asp Leu Lys Ala
65                  70                  75                  80

His Lys Glu Leu Ile Leu His Ala Lys Lys Cys Asn Ile Ala Phe Leu
                85                  90                  95

Ser Thr Pro Phe Asp Leu Glu Ser Val Asp Leu Leu Asn Glu Leu Gly
            100                 105                 110

Leu Lys Ile Phe Lys Ile Pro Ser Gly Glu Ile Thr Asn Leu Pro Tyr
        115                 120                 125

Leu Lys Lys Ile Ala Lys Leu Asn Lys Lys Ile Ile Leu Ser Thr Gly
    130                 135                 140

Met Ala Asn Leu Gly Glu Ile Glu Glu Ala Leu Asn Val Leu Cys Lys
145                 150                 155                 160

Asn Gly Ala Lys Arg Gln Asn Ile Thr Leu Leu His Cys Thr Thr Glu
                165                 170                 175

Tyr Pro Ala Pro Phe Asn Glu Val Asn Leu Lys Ala Met Gln Ser Leu
            180                 185                 190

Lys Asp Ala Phe Lys Leu Asp Val Gly Tyr Ser Asp His Thr Arg Gly
        195                 200                 205

Ile His Ile Ser Leu Ala Ala Val Ala Leu Gly Ala Cys Val Ile Glu
    210                 215                 220

Lys His Phe Thr Leu Asp Lys Asn Met Ser Gly Pro Asp His Lys Ala
225                 230                 235                 240

Ser Leu Glu Pro Gln Glu Leu Lys Met Leu Cys Thr Gln Ile Arg Gln
                245                 250                 255

Ile Gln Lys Ala Met Gly Asp Gly Ile Lys Lys Ala Ser Lys Ser Glu
            260                 265                 270

Gln Lys Asn Ile Asn Ile Val Arg Lys Ser Leu Val Ala Lys Lys Asp
        275                 280                 285
```

Ile Lys Lys Gly Glu Ile Phe Ser Glu Gly Asn Leu Thr Thr Lys Arg
    290                 295                 300
Pro Ala Asn Gly Ile Ser Ala Met Arg Tyr Glu Glu Phe Leu Gly Lys
305                 310                 315                 320
Ile Ala Thr Lys Asn Tyr Lys Glu Asp Glu Leu Ile Arg Glu
                325                 330

<210> SEQ ID NO 10
<211> LENGTH: 356
<212> TYPE: PRT
<213> ORGANISM: L. pneumophila

<400> SEQUENCE: 10

Met Gly Ser Asn Arg Lys Ile Asn Gly Ile Lys Pro Arg Gly Ser Ser
1               5                   10                  15

Met Thr Cys Phe Ile Ile Ala Glu Ala Gly Val Asn His Asn Gly Asp
            20                  25                  30

Leu Gln Leu Ala Lys Glu Leu Val Tyr Ala Ala Lys Glu Ser Gly Ala
        35                  40                  45

Asp Ala Val Lys Phe Gln Thr Phe Lys Ala Asp Thr Leu Val Asn Lys
    50                  55                  60

Thr Val Glu Lys Ala Glu Tyr Gln Lys Asn Asn Ala Pro Glu Ser Ser
65                  70                  75                  80

Thr Gln Tyr Glu Met Leu Lys Ala Leu Glu Leu Ser Glu Glu Asp His
                85                  90                  95

Tyr Leu Leu Ser Glu Leu Ala Asn Ser Leu Gly Ile Glu Phe Met Ser
            100                 105                 110

Thr Gly Phe Asp Glu Gln Ser Ile Asp Phe Leu Ile Ser Leu Gly Val
        115                 120                 125

Lys Arg Leu Lys Ile Pro Ser Gly Glu Ile Thr Asn Val Pro Tyr Leu
    130                 135                 140

Gln His Cys Ala Ser Lys Lys Leu Pro Leu Ile Ile Ser Thr Gly Met
145                 150                 155                 160

Cys Asp Leu Gln Glu Val Arg Val Ala Ile Asp Thr Val Lys Pro Tyr
                165                 170                 175

Tyr Gly Asn Ser Leu Ser Asp Tyr Leu Val Leu Leu His Cys Thr Ser
            180                 185                 190

Asn Tyr Pro Ala Ser Tyr Gln Asp Val Asn Leu Lys Ala Met Gln Thr
        195                 200                 205

Leu Ala Asp Glu Phe Gln Leu Pro Val Gly Tyr Ser Asp His Thr Leu
    210                 215                 220

Gly Ile Leu Val Pro Thr Leu Ala Val Gly Met Gly Ala Cys Val Ile
225                 230                 235                 240

Glu Lys His Phe Thr Met Asp Lys Ser Leu Pro Gly Pro Asp His Leu
                245                 250                 255

Ala Ser Met Asp Pro Glu Glu Met Lys Asn Leu Val Gln Ser Ile Arg
            260                 265                 270

Asp Ala Glu Thr Val Leu Gly Ser Gly Glu Lys Lys Pro Ser Asp Asn
        275                 280                 285

Glu Leu Pro Ile Arg Ala Leu Val Arg Arg Ser Ile Thr Leu Arg Arg
    290                 295                 300

Asp Leu Val Lys Gly Ala Gln Ile Ser Lys Glu Asp Leu Ile Leu Leu
305                 310                 315                 320

Arg Pro Gly Thr Gly Ile Ala Pro Ser Glu Ile Ser Asn Ile Val Gly
                325                 330                 335

Ser Arg Leu Ser Met Asn Leu Ser Ala Gly Thr Thr Leu Leu Trp Glu
340 345 350

His Ile Glu Ala
355

<210> SEQ ID NO 11
<211> LENGTH: 377
<212> TYPE: PRT
<213> ORGANISM: L. pneumophila

<400> SEQUENCE: 11

Met Ile Arg Lys Ile Ile Tyr Val Thr Gly Thr Arg Ala Asp Tyr Gly
1 5 10 15

Leu Met Arg Glu Val Leu Lys Arg Leu His Gln Ser Glu Asp Ile Asp
20 25 30

Leu Ser Ile Cys Val Thr Gly Met His Leu Asp Ala Leu Tyr Gly Asn
35 40 45

Thr Val Asn Glu Ile Lys Ala Asp Gln Phe Ser Ile Cys Gly Ile Ile
50 55 60

Pro Val Asp Leu Ala Asn Ala Gln His Ser Ser Met Ala Lys Ala Ile
65 70 75 80

Gly His Glu Leu Leu Gly Phe Thr Glu Val Phe Glu Ser Glu Thr Pro
85 90 95

Asp Val Val Leu Leu Leu Gly Asp Arg Gly Glu Met Leu Ala Ala Ala
100 105 110

Ile Ala Ala Ile His Leu Asn Ile Pro Val Val His Leu His Gly Gly
115 120 125

Glu Arg Ser Gly Thr Val Asp Glu Met Val Arg His Ala Ile Ser Lys
130 135 140

Leu Ser His Tyr His Phe Val Ala Thr Glu Ala Ser Lys Gln Arg Leu
145 150 155 160

Ile Arg Met Gly Glu Lys Glu Glu Thr Ile Phe Gln Val Gly Ala Pro
165 170 175

Gly Leu Asp Glu Ile Met Gln Tyr Lys Thr Ser Thr Arg Asp Val Phe
180 185 190

Asn Gln Arg Tyr Gly Phe Asp Pro Asp Lys Lys Ile Cys Leu Leu Ile
195 200 205

Tyr His Pro Val Val Gln Glu Val Asp Ser Ile Lys Ile Gln Phe Gln
210 215 220

Ser Val Ile Gln Ala Ala Leu Ala Thr Asn Leu Gln Ile Ile Cys Leu
225 230 235 240

Glu Pro Asn Ser Asp Thr Gly Gly His Leu Ile Arg Glu Val Ile Gln
245 250 255

Glu Tyr Ile Asp His Pro Asp Val Arg Ile Ile Lys His Leu His Arg
260 265 270

Pro Glu Phe Ile Asp Cys Leu Ala Asn Ser Asp Val Met Leu Gly Asn
275 280 285

Ser Ser Ser Gly Ile Ile Glu Ala Ala Ser Phe Asn Leu Asn Val Val
290 295 300

Asn Val Gly Ser Arg Gln Asn Leu Arg Glu Arg Ser Asp Asn Val Ile
305 310 315 320

Asp Val Asp Val Thr Tyr Asp Ala Ile Leu Thr Gly Leu Arg Glu Ala
325 330 335

Leu Asn Lys Pro Lys Ile Lys Tyr Ser Asn Cys Tyr Gly Asp Gly Lys

```
                    340                 345                 350
Thr Ser Glu Arg Cys Tyr Gln Leu Leu Lys Thr Ile Pro Leu His Ser
            355                 360                 365
Gln Ile Leu Asn Lys Cys Asn Ala Tyr
            370                 375

<210> SEQ ID NO 12
<211> LENGTH: 557
<212> TYPE: PRT
<213> ORGANISM: S. cerevisiae

<400> SEQUENCE: 12

Met Lys Val Asp Tyr Glu Gln Leu Cys Lys Leu Tyr Asp Asp Met Cys
1               5                   10                  15
Arg Thr Lys Asn Val Gln Phe Ser Tyr Gly Thr Ala Gly Phe Arg Thr
            20                  25                  30
Leu Ala Lys Asn Leu Asp Thr Val Met Phe Ser Thr Gly Ile Leu Ala
            35                  40                  45
Val Leu Arg Ser Leu Lys Leu Gln Gly Gln Tyr Val Gly Val Met Ile
        50                  55                  60
Thr Ala Ser His Asn Pro Tyr Gln Asp Asn Gly Val Lys Ile Val Glu
65                  70                  75                  80
Pro Asp Gly Ser Met Leu Leu Ala Thr Trp Glu Pro Tyr Ala Met Gln
                85                  90                  95
Leu Ala Asn Ala Ala Ser Phe Ala Thr Asn Phe Glu Glu Phe Arg Val
            100                 105                 110
Glu Leu Ala Lys Leu Ile Glu His Glu Lys Ile Asp Leu Asn Thr Thr
        115                 120                 125
Val Val Pro His Ile Val Val Gly Arg Asp Ser Arg Glu Ser Ser Pro
130                 135                 140
Tyr Leu Leu Arg Cys Leu Thr Ser Ser Met Ala Ser Val Phe His Ala
145                 150                 155                 160
Gln Val Leu Asp Leu Gly Cys Val Thr Thr Pro Gln Leu His Tyr Ile
                165                 170                 175
Thr Asp Leu Ser Asn Arg Arg Lys Leu Glu Gly Asp Thr Ala Pro Val
            180                 185                 190
Ala Thr Glu Arg Asp Tyr Tyr Ser Phe Phe Ile Gly Ala Phe Asn Glu
        195                 200                 205
Leu Phe Ala Thr Tyr Gln Leu Glu Lys Arg Leu Ser Val Pro Lys Leu
    210                 215                 220
Phe Ile Asp Thr Ala Asn Gly Ile Gly Gly Pro Gln Leu Lys Lys Leu
225                 230                 235                 240
Leu Ala Ser Glu Asp Trp Asp Val Pro Ala Glu Gln Val Glu Val Ile
                245                 250                 255
Asn Asp Arg Ser Asp Val Pro Glu Leu Leu Asn Phe Glu Cys Gly Ala
            260                 265                 270
Asp Tyr Val Lys Thr Asn Gln Arg Leu Pro Lys Gly Leu Ser Pro Ser
        275                 280                 285
Ser Phe Asp Ser Leu Tyr Cys Ser Phe Asp Gly Asp Ala Asp Arg Val
    290                 295                 300
Val Phe Tyr Tyr Val Asp Ser Gly Ser Lys Phe His Leu Leu Asp Gly
305                 310                 315                 320
Asp Lys Ile Ser Thr Leu Phe Ala Lys Phe Leu Ser Lys Gln Leu Glu
                325                 330                 335
```

```
Leu Ala His Leu Glu His Ser Leu Lys Ile Gly Val Val Gln Thr Ala
                340                 345                 350
Tyr Ala Asn Gly Ser Ser Thr Ala Tyr Ile Lys Asn Thr Leu His Cys
            355                 360                 365
Pro Val Ser Cys Thr Lys Thr Gly Val Lys His Leu His His Glu Ala
        370                 375                 380
Ala Thr Gln Tyr Asp Ile Gly Ile Tyr Phe Glu Ala Asn Gly His Gly
385                 390                 395                 400
Thr Ile Ile Phe Ser Gly Lys Phe His Arg Thr Ile Lys Ser Glu Leu
                405                 410                 415
Ser Lys Ser Lys Leu Asn Gly Asp Thr Leu Ala Leu Arg Thr Leu Lys
            420                 425                 430
Cys Phe Ser Glu Leu Ile Asn Gln Thr Val Gly Asp Ala Ile Ser Asp
        435                 440                 445
Met Leu Ala Val Leu Ala Thr Leu Ala Ile Leu Lys Met Ser Pro Met
450                 455                 460
Asp Trp Asp Glu Glu Tyr Thr Asp Leu Pro Asn Lys Leu Val Lys Cys
465                 470                 475                 480
Ile Val Pro Asp Arg Ser Ile Phe Gln Thr Thr Asp Gln Arg Lys
                485                 490                 495
Leu Leu Asn Pro Val Gly Leu Gln Asp Lys Ile Asp Leu Val Val Ala
            500                 505                 510
Lys Tyr Pro Met Gly Arg Ser Phe Val Arg Ala Ser Gly Thr Glu Asp
        515                 520                 525
Ala Val Arg Val Tyr Ala Glu Cys Lys Asp Ser Ser Lys Leu Gly Gln
530                 535                 540
Phe Cys Asp Glu Val Val Glu His Val Lys Ala Ser Ala
545                 550                 555

<210> SEQ ID NO 13
<211> LENGTH: 477
<212> TYPE: PRT
<213> ORGANISM: S. cerevisiae

<400> SEQUENCE: 13

Met Thr Asp Thr Lys Gln Leu Phe Ile Glu Ala Gly Gln Ser Gln Leu
1               5                   10                  15
Phe His Asn Trp Glu Ser Leu Ser Arg Lys Asp Gln Glu Glu Leu Leu
                20                  25                  30
Ser Asn Leu Glu Gln Ile Ser Ser Lys Arg Ser Pro Ala Lys Leu Leu
            35                  40                  45
Glu Asp Cys Gln Asn Ala Ile Lys Phe Ser Leu Ala Asn Ser Ser Lys
        50                  55                  60
Asp Thr Gly Val Glu Ile Ser Pro Leu Pro Thr Ser Tyr Glu Ser
65                  70                  75                  80
Leu Ile Gly Asn Ser Lys Lys Glu Asn Glu Tyr Trp Arg Leu Gly Leu
                85                  90                  95
Glu Ala Ile Gly Lys Gly Glu Val Ala Val Ile Leu Met Ala Gly Gly
            100                 105                 110
Gln Gly Thr Arg Leu Gly Ser Ser Gln Pro Lys Gly Cys Tyr Asp Ile
        115                 120                 125
Gly Leu Pro Ser Lys Lys Ser Leu Phe Gln Ile Gln Ala Glu Lys Leu
    130                 135                 140
Ile Arg Leu Gln Asp Met Val Lys Asp Lys Lys Val Glu Ile Pro Trp
145                 150                 155                 160
```

Tyr Ile Met Thr Ser Gly Pro Thr Arg Ala Thr Glu Ala Tyr Phe
                165                 170                 175

Gln Glu His Asn Tyr Phe Gly Leu Asn Lys Glu Gln Ile Thr Phe Phe
            180                 185                 190

Asn Gln Gly Thr Leu Pro Ala Phe Asp Leu Thr Gly Lys His Phe Leu
        195                 200                 205

Met Lys Asp Pro Val Asn Leu Ser Gln Ser Pro Asp Gly Asn Gly Gly
    210                 215                 220

Leu Tyr Arg Ala Ile Lys Glu Asn Lys Leu Asn Glu Asp Phe Asp Arg
225                 230                 235                 240

Arg Gly Ile Lys His Val Tyr Met Tyr Cys Val Asp Asn Val Leu Ser
                245                 250                 255

Lys Ile Ala Asp Pro Val Phe Ile Gly Phe Ala Ile Lys His Gly Phe
            260                 265                 270

Glu Leu Ala Thr Lys Ala Val Arg Lys Arg Asp Ala His Glu Ser Val
        275                 280                 285

Gly Leu Ile Ala Thr Lys Asn Glu Lys Pro Cys Val Ile Glu Tyr Ser
    290                 295                 300

Glu Ile Ser Asn Glu Leu Ala Glu Ala Lys Asp Lys Asp Gly Leu Leu
305                 310                 315                 320

Lys Leu Arg Ala Gly Asn Ile Val Asn His Tyr Tyr Leu Val Asp Leu
                325                 330                 335

Leu Lys Arg Asp Leu Asp Gln Trp Cys Glu Asn Met Pro Tyr His Ile
            340                 345                 350

Ala Lys Lys Lys Ile Pro Ala Tyr Asp Ser Val Thr Gly Lys Tyr Thr
        355                 360                 365

Lys Pro Thr Glu Pro Asn Gly Ile Lys Leu Glu Gln Phe Ile Phe Asp
    370                 375                 380

Val Phe Asp Thr Val Pro Leu Asn Lys Phe Gly Cys Leu Glu Val Asp
385                 390                 395                 400

Arg Cys Lys Glu Phe Ser Pro Leu Lys Asn Gly Pro Gly Ser Lys Asn
                405                 410                 415

Asp Asn Pro Glu Thr Ser Arg Leu Ala Tyr Leu Lys Leu Gly Thr Ser
            420                 425                 430

Trp Leu Glu Asp Ala Gly Ala Ile Val Lys Asp Gly Val Leu Val Glu
        435                 440                 445

Val Ser Ser Lys Leu Ser Tyr Ala Gly Glu Asn Leu Ser Gln Phe Lys
    450                 455                 460

Gly Lys Val Phe Asp Arg Ser Gly Ile Val Leu Glu Lys
465                 470                 475

<210> SEQ ID NO 14
<211> LENGTH: 496
<212> TYPE: PRT
<213> ORGANISM: E. Coli

<400> SEQUENCE: 14

Met Ser Thr Thr Thr Gln Asn Ile Pro Trp Tyr Arg His Leu Asn Arg
1               5                   10                  15

Ala Gln Trp Arg Ala Phe Ser Ala Ala Trp Leu Gly Tyr Leu Leu Asp
            20                  25                  30

Gly Phe Asp Phe Val Leu Ile Ala Leu Val Leu Thr Glu Val Gln Gly
        35                  40                  45

Glu Phe Gly Leu Thr Thr Val Gln Ala Ala Ser Leu Ile Ser Ala Ala

```
              50                  55                  60
    Phe Ile Ser Arg Trp Phe Gly Gly Leu Met Leu Gly Ala Met Gly Asp
     65                  70                  75                  80

Arg Tyr Gly Arg Arg Leu Ala Met Val Thr Ser Ile Val Leu Phe Ser
                     85                  90                  95

Ala Gly Thr Leu Ala Cys Gly Phe Ala Pro Gly Tyr Ile Thr Met Phe
                100                 105                 110

Ile Ala Arg Leu Val Ile Gly Met Gly Met Ala Gly Glu Tyr Gly Ser
                115                 120                 125

Ser Ala Thr Tyr Val Ile Glu Ser Trp Pro Lys His Leu Arg Asn Lys
                130                 135                 140

Ala Ser Gly Phe Leu Ile Ser Gly Phe Ser Val Gly Ala Val Val Ala
    145                 150                 155                 160

Ala Gln Val Tyr Ser Leu Val Val Pro Val Trp Gly Trp Arg Ala Leu
                    165                 170                 175

Phe Phe Ile Gly Ile Leu Pro Ile Ile Phe Ala Leu Trp Leu Arg Lys
                    180                 185                 190

Asn Ile Pro Glu Ala Glu Asp Trp Lys Glu Lys His Ala Gly Lys Ala
                    195                 200                 205

Pro Val Arg Thr Met Val Asp Ile Leu Tyr Arg Gly Glu His Arg Ile
                    210                 215                 220

Ala Asn Ile Val Met Thr Leu Ala Ala Ala Thr Ala Leu Trp Phe Cys
    225                 230                 235                 240

Phe Ala Gly Asn Leu Gln Asn Ala Ala Ile Val Ala Val Leu Gly Leu
                    245                 250                 255

Leu Cys Ala Ala Ile Phe Ile Ser Phe Met Val Gln Ser Ala Gly Lys
                    260                 265                 270

Arg Trp Pro Thr Gly Val Met Leu Met Val Val Leu Phe Ala Phe
                    275                 280                 285

Leu Tyr Ser Trp Pro Ile Gln Ala Leu Leu Pro Thr Tyr Leu Lys Thr
                    290                 295                 300

Asp Leu Ala Tyr Asn Pro His Thr Val Ala Asn Val Leu Phe Phe Ser
    305                 310                 315                 320

Gly Phe Gly Ala Ala Val Gly Cys Cys Val Gly Gly Phe Leu Gly Asp
                    325                 330                 335

Trp Leu Gly Thr Arg Lys Ala Tyr Val Cys Ser Leu Leu Ala Ser Gln
                    340                 345                 350

Leu Leu Ile Ile Pro Val Phe Ala Ile Gly Gly Ala Asn Val Trp Val
                    355                 360                 365

Leu Gly Leu Leu Leu Phe Phe Gln Gln Met Leu Gly Gln Gly Ile Ala
                    370                 375                 380

Gly Ile Leu Pro Lys Leu Ile Gly Gly Tyr Phe Asp Thr Asp Gln Arg
    385                 390                 395                 400

Ala Ala Gly Leu Gly Phe Thr Tyr Asn Val Gly Ala Leu Gly Gly Ala
                    405                 410                 415

Leu Ala Pro Ile Ile Gly Ala Leu Ile Ala Gln Arg Leu Asp Leu Gly
                    420                 425                 430

Thr Ala Leu Ala Ser Leu Ser Phe Ser Leu Thr Phe Val Val Ile Leu
                    435                 440                 445

Leu Ile Gly Leu Asp Met Pro Ser Arg Val Gln Arg Trp Leu Arg Pro
                    450                 455                 460

Glu Ala Leu Arg Thr His Asp Ala Ile Asp Gly Lys Pro Phe Ser Gly
    465                 470                 475                 480
```

Ala Val Pro Phe Gly Ser Ala Lys Asn Asp Leu Val Lys Thr Lys Ser
            485                 490                 495

<210> SEQ ID NO 15
<211> LENGTH: 297
<212> TYPE: PRT
<213> ORGANISM: E. Coli

<400> SEQUENCE: 15

Met Ala Thr Asn Leu Arg Gly Val Met Ala Ala Leu Leu Thr Pro Phe
1               5                   10                  15

Asp Gln Gln Gln Ala Leu Asp Lys Ala Ser Leu Arg Arg Leu Val Gln
            20                  25                  30

Phe Asn Ile Gln Gln Gly Ile Asp Gly Leu Tyr Val Gly Gly Ser Thr
        35                  40                  45

Gly Glu Ala Phe Val Gln Ser Leu Ser Glu Arg Glu Gln Val Leu Glu
    50                  55                  60

Ile Val Ala Glu Glu Ala Lys Gly Lys Ile Lys Leu Ile Ala His Val
65                  70                  75                  80

Gly Cys Val Ser Thr Ala Glu Ser Gln Gln Leu Ala Ala Ser Ala Lys
                85                  90                  95

Arg Tyr Gly Phe Asp Ala Val Ser Ala Val Thr Pro Phe Tyr Tyr Pro
            100                 105                 110

Phe Ser Phe Glu Glu His Cys Asp His Tyr Arg Ala Ile Ile Asp Ser
        115                 120                 125

Ala Asp Gly Leu Pro Met Val Val Tyr Asn Ile Pro Ala Leu Ser Gly
    130                 135                 140

Val Lys Leu Thr Leu Asp Gln Ile Asn Thr Leu Val Thr Leu Pro Gly
145                 150                 155                 160

Val Gly Ala Leu Lys Gln Thr Ser Gly Asp Leu Tyr Gln Met Glu Gln
                165                 170                 175

Ile Arg Arg Glu His Pro Asp Leu Val Leu Tyr Asn Gly Tyr Asp Glu
            180                 185                 190

Ile Phe Ala Ser Gly Leu Leu Ala Gly Ala Asp Gly Gly Ile Gly Ser
        195                 200                 205

Thr Tyr Asn Ile Met Gly Trp Arg Tyr Gln Gly Ile Val Lys Ala Leu
    210                 215                 220

Lys Glu Gly Asp Ile Gln Thr Ala Gln Lys Leu Gln Thr Glu Cys Asn
225                 230                 235                 240

Lys Val Ile Asp Leu Leu Ile Lys Thr Gly Val Phe Arg Gly Leu Lys
                245                 250                 255

Thr Val Leu His Tyr Met Asp Val Val Ser Val Pro Leu Cys Arg Lys
            260                 265                 270

Pro Phe Gly Pro Val Asp Glu Lys Tyr Leu Pro Glu Leu Lys Ala Leu
        275                 280                 285

Ala Gln Gln Leu Met Gln Glu Arg Gly
    290                 295

<210> SEQ ID NO 16
<211> LENGTH: 382
<212> TYPE: PRT
<213> ORGANISM: E. Coli

<400> SEQUENCE: 16

Met Tyr Ala Leu Thr Gln Gly Arg Ile Phe Thr Gly His Glu Phe Leu
1               5                   10                  15

Asp Asp His Ala Val Ile Ala Asp Gly Leu Ile Lys Ser Val Cys
            20                  25                  30

Pro Val Ala Glu Leu Pro Pro Glu Ile Glu Gln Arg Ser Leu Asn Gly
        35                  40                  45

Ala Ile Leu Ser Pro Gly Phe Ile Asp Val Gln Leu Asn Gly Cys Gly
    50                  55                  60

Gly Val Gln Phe Asn Asp Thr Ala Glu Ala Val Ser Val Glu Thr Leu
65                  70                  75                  80

Glu Ile Met Gln Lys Ala Asn Glu Lys Ser Gly Cys Thr Asn Tyr Leu
                85                  90                  95

Pro Thr Leu Ile Thr Thr Ser Asp Glu Leu Met Lys Gln Gly Val Arg
        100                 105                 110

Val Met Arg Glu Tyr Leu Ala Lys His Pro Asn Gln Ala Leu Gly Leu
    115                 120                 125

His Leu Glu Gly Pro Trp Leu Asn Leu Val Lys Lys Gly Thr His Asn
130                 135                 140

Pro Asn Phe Val Arg Lys Pro Asp Ala Ala Leu Val Asp Phe Leu Cys
                150                 155                 160
145

Glu Asn Ala Asp Val Ile Thr Lys Val Thr Leu Ala Pro Glu Met Val
            165                 170                 175

Pro Ala Glu Val Ile Ser Lys Leu Ala Asn Ala Gly Ile Val Val Ser
        180                 185                 190

Ala Gly His Ser Asn Ala Thr Leu Lys Glu Lys Ala Gly Phe Arg
    195                 200                 205

Ala Gly Ile Thr Phe Ala Thr His Leu Tyr Asn Ala Met Pro Tyr Ile
    210                 215                 220

Thr Gly Arg Glu Pro Gly Leu Ala Gly Ala Ile Leu Asp Glu Ala Asp
225                 230                 235                 240

Ile Tyr Cys Gly Ile Ile Ala Asp Gly Leu His Val Asp Tyr Ala Asn
                245                 250                 255

Ile Arg Asn Ala Lys Arg Leu Lys Gly Asp Lys Leu Cys Leu Val Thr
            260                 265                 270

Asp Ala Thr Ala Pro Ala Gly Ala Asn Ile Glu Gln Phe Ile Phe Ala
        275                 280                 285

Gly Lys Thr Ile Tyr Tyr Arg Asn Gly Leu Cys Val Asp Glu Asn Gly
    290                 295                 300

Thr Leu Ser Gly Ser Ser Leu Thr Met Ile Glu Gly Val Arg Asn Leu
305                 310                 315                 320

Val Glu His Cys Gly Ile Ala Leu Asp Glu Val Leu Arg Met Ala Thr
                325                 330                 335

Leu Tyr Pro Ala Arg Ala Ile Gly Val Glu Lys Arg Leu Gly Thr Leu
            340                 345                 350

Ala Ala Gly Lys Val Ala Asn Leu Thr Ala Phe Thr Pro Asp Phe Lys
        355                 360                 365

Ile Thr Lys Thr Ile Val Asn Gly Asn Glu Val Val Thr Gln
    370                 375                 380

<210> SEQ ID NO 17
<211> LENGTH: 229
<212> TYPE: PRT
<213> ORGANISM: E. Coli

<400> SEQUENCE: 17

Met Ser Leu Leu Ala Gln Leu Asp Gln Lys Ile Ala Ala Asn Gly Gly

```
            1               5                      10                       15
Leu Ile Val Ser Cys Gln Pro Val Pro Asp Ser Pro Leu Asp Lys Pro
                20                      25                      30

Glu Ile Val Ala Ala Met Ala Leu Ala Ala Glu Gln Ala Gly Ala Val
                35                      40                      45

Ala Ile Arg Ile Glu Gly Val Ala Asn Leu Gln Ala Thr Arg Ala Val
            50                      55                      60

Val Ser Val Pro Ile Ile Gly Ile Val Lys Arg Asp Leu Glu Asp Ser
65                      70                      75                      80

Pro Val Arg Ile Thr Ala Tyr Ile Glu Asp Val Asp Ala Leu Ala Gln
                        85                      90                      95

Ala Gly Ala Asp Ile Ile Ala Ile Asp Gly Thr Asp Arg Pro Arg Pro
                    100                     105                     110

Val Pro Val Glu Thr Leu Leu Ala Arg Ile His His Gly Leu Leu
                    115                     120                     125

Ala Met Thr Asp Cys Ser Thr Pro Glu Asp Gly Leu Ala Cys Gln Lys
            130                     135                     140

Leu Gly Ala Glu Ile Ile Gly Thr Thr Leu Ser Gly Tyr Thr Thr Pro
145                     150                     155                     160

Glu Thr Pro Glu Glu Pro Asp Leu Ala Leu Val Lys Thr Leu Ser Asp
                    165                     170                     175

Ala Gly Cys Arg Val Ile Ala Glu Gly Arg Tyr Asn Thr Pro Ala Gln
                180                     185                     190

Ala Ala Asp Ala Met Arg His Gly Ala Trp Ala Val Thr Val Gly Ser
            195                     200                     205

Ala Ile Thr Arg Leu Glu His Ile Cys Gln Trp Tyr Asn Thr Ala Met
        210                     215                     220

Lys Lys Ala Val Leu
225

<210> SEQ ID NO 18
<211> LENGTH: 367
<212> TYPE: PRT
<213> ORGANISM: E. Coli

<400> SEQUENCE: 18

Met Asn Leu Leu Thr Val Ser Thr Asp Leu Ile Ser Ile Phe Leu Phe
1               5                       10                      15

Thr Thr Leu Phe Leu Phe Phe Ala Arg Lys Val Ala Lys Lys Val Gly
                20                      25                      30

Leu Val Asp Lys Pro Asn Phe Arg Lys Arg His Gln Gly Leu Ile Pro
                35                      40                      45

Leu Val Gly Gly Ile Ser Val Tyr Ala Gly Ile Cys Phe Thr Phe Gly
            50                      55                      60

Ile Val Asp Tyr Tyr Ile Pro His Ala Ser Leu Tyr Leu Ala Cys Ala
65                      70                      75                      80

Gly Val Leu Val Phe Ile Gly Ala Leu Asp Asp Arg Phe Asp Ile Ser
                        85                      90                      95

Val Lys Ile Arg Ala Thr Ile Gln Ala Ala Val Gly Ile Val Met Met
                    100                     105                     110

Val Phe Gly Lys Leu Tyr Leu Ser Ser Leu Gly Tyr Ile Phe Gly Ser
                115                     120                     125

Trp Glu Met Val Leu Gly Pro Phe Gly Tyr Phe Leu Thr Leu Phe Ala
            130                     135                     140
```

Val Trp Ala Ala Ile Asn Ala Phe Asn Met Val Asp Gly Ile Asp Gly
145                 150                 155                 160

Leu Leu Gly Gly Leu Ser Cys Val Ser Phe Ala Ala Ile Gly Met Ile
            165                 170                 175

Leu Trp Phe Asp Gly Gln Thr Ser Leu Ala Ile Trp Cys Phe Ala Met
        180                 185                 190

Ile Ala Ala Ile Leu Pro Tyr Ile Met Leu Asn Leu Gly Ile Leu Gly
        195                 200                 205

Arg Arg Tyr Lys Val Phe Met Gly Asp Ala Gly Ser Thr Leu Ile Gly
        210                 215                 220

Phe Thr Val Ile Trp Ile Leu Leu Glu Thr Thr Gln Gly Lys Thr His
225                 230                 235                 240

Pro Ile Ser Pro Val Thr Ala Leu Trp Ile Ile Ala Ile Pro Leu Met
                245                 250                 255

Asp Met Val Ala Ile Met Tyr Arg Arg Leu Arg Lys Gly Met Ser Pro
            260                 265                 270

Phe Ser Pro Asp Arg Gln His Ile His His Leu Ile Met Arg Ala Gly
        275                 280                 285

Phe Thr Ser Arg Gln Ala Phe Val Leu Ile Thr Leu Ala Ala Ala Leu
        290                 295                 300

Leu Ala Ser Ile Gly Val Leu Ala Glu Tyr Ser His Phe Val Pro Glu
305                 310                 315                 320

Trp Val Met Leu Val Leu Phe Leu Leu Ala Phe Phe Leu Tyr Gly Tyr
                325                 330                 335

Cys Ile Lys Arg Ala Trp Lys Val Ala Arg Phe Ile Lys Arg Val Lys
            340                 345                 350

Arg Arg Leu Arg Arg Asn Arg Gly Gly Ser Pro Asn Leu Thr Lys
        355                 360                 365

<210> SEQ ID NO 19
<211> LENGTH: 32
<212> TYPE: DNA
<213> ORGANISM: Artificial sequence
<220> FEATURE:
<223> OTHER INFORMATION: pseB primer

<400> SEQUENCE: 19
gcagcatatg ccaaatcatc aaaacatgct ag                                   32

<210> SEQ ID NO 20
<211> LENGTH: 40
<212> TYPE: DNA
<213> ORGANISM: Artificial sequence
<220> FEATURE:
<223> OTHER INFORMATION: pseB primer

<400> SEQUENCE: 20
gcaggaattc tcataataat ttcaacaaat catcaggctc                           40

<210> SEQ ID NO 21
<211> LENGTH: 43
<212> TYPE: DNA
<213> ORGANISM: Artificial sequence
<220> FEATURE:
<223> OTHER INFORMATION: pseB primer

<400> SEQUENCE: 21
ccatttagcc ctagagttcg aagacttttt catcattcag ccc                       43

```
<210> SEQ ID NO 22
<211> LENGTH: 43
<212> TYPE: DNA
<213> ORGANISM: Artificial sequence
<220> FEATURE:
<223> OTHER INFORMATION: pseB primer

<400> SEQUENCE: 22
gggctgaatg atgaaaaagt cttcgaactc tagggctaaa tgg          43

<210> SEQ ID NO 23
<211> LENGTH: 31
<212> TYPE: DNA
<213> ORGANISM: Artificial sequence
<220> FEATURE:
<223> OTHER INFORMATION: pseC primer

<400> SEQUENCE: 23
gcagcatatg aaagagtttg cttatagcga g                       31

<210> SEQ ID NO 24
<211> LENGTH: 36
<212> TYPE: DNA
<213> ORGANISM: Artificial sequence
<220> FEATURE:
<223> OTHER INFORMATION: pseC primer

<400> SEQUENCE: 24
gcaggaattc tcattctatt ttaaaactct caaaag                  36

<210> SEQ ID NO 25
<211> LENGTH: 47
<212> TYPE: DNA
<213> ORGANISM: Artificial sequence
<220> FEATURE:
<223> OTHER INFORMATION: pseH primer

<400> SEQUENCE: 25
gcagcatatg aaaaaaaatt attcttataa aaatatccaa gcgattg       47

<210> SEQ ID NO 26
<211> LENGTH: 42
<212> TYPE: DNA
<213> ORGANISM: Artificial sequence
<220> FEATURE:
<223> OTHER INFORMATION: pseH primer

<400> SEQUENCE: 26
gcaggaattc ctaaagtttt agaagagatt gatcattata tc           42

<210> SEQ ID NO 27
<211> LENGTH: 34
<212> TYPE: DNA
<213> ORGANISM: Artificial sequence
<220> FEATURE:
<223> OTHER INFORMATION: pseG primer

<400> SEQUENCE: 27
ggaccatatg aaagtgcttt ttagaagcga tagc                    34

<210> SEQ ID NO 28
<211> LENGTH: 37
<212> TYPE: DNA
<213> ORGANISM: Artificial sequence
<220> FEATURE:
<223> OTHER INFORMATION: pseG primer
```

<400> SEQUENCE: 28
ggacgaattc tcaatactta tactccactt catacccc					37

<210> SEQ ID NO 29
<211> LENGTH: 31
<212> TYPE: DNA
<213> ORGANISM: Artificial sequence
<220> FEATURE:
<223> OTHER INFORMATION: pseI primer

<400> SEQUENCE: 29
gcagcatatg ttacaacccc ctaaaattgt c					31

<210> SEQ ID NO 30
<211> LENGTH: 34
<212> TYPE: DNA
<213> ORGANISM: Artificial sequence
<220> FEATURE:
<223> OTHER INFORMATION: pseI primer

<400> SEQUENCE: 30
gcaggaattc ctacaatgag cgttctatat catc					34

<210> SEQ ID NO 31
<211> LENGTH: 37
<212> TYPE: DNA
<213> ORGANISM: Artificial sequence
<220> FEATURE:
<223> OTHER INFORMATION: pgIF primer

<400> SEQUENCE: 31
gcagcatatg attttttata aaagcaaaag attagca					37

<210> SEQ ID NO 32
<211> LENGTH: 40
<212> TYPE: DNA
<213> ORGANISM: Artificial sequence
<220> FEATURE:
<223> OTHER INFORMATION: pgIF primer

<400> SEQUENCE: 32
gcaggaattc ttatacacct tctttattgt gtttaaattc					40

<210> SEQ ID NO 33
<211> LENGTH: 47
<212> TYPE: DNA
<213> ORGANISM: Artificial sequence
<220> FEATURE:
<223> OTHER INFORMATION: pgIE primer

<400> SEQUENCE: 33
gcagcatatg agatttttc tttctcctcc gcacatgggt ggtaatg					47

<210> SEQ ID NO 34
<211> LENGTH: 43
<212> TYPE: DNA
<213> ORGANISM: Artificial sequence
<220> FEATURE:
<223> OTHER INFORMATION: pgIE primer

<400> SEQUENCE: 34
gcaggaattc ttaagccttt atgctcttta agatcagttt tga					43

<210> SEQ ID NO 35
<211> LENGTH: 39

<212> TYPE: DNA
<213> ORGANISM: Artificial sequence
<220> FEATURE:
<223> OTHER INFORMATION: pgID primer

<400> SEQUENCE: 35
gcagcatatg gcaagaactg aaaaaattta tatttatgg                                39

<210> SEQ ID NO 36
<211> LENGTH: 34
<212> TYPE: DNA
<213> ORGANISM: Artificial sequence
<220> FEATURE:
<223> OTHER INFORMATION: pgID primer

<400> SEQUENCE: 36
gcaggaattc ttacatcctt tttgcaggta ctcc                                     34

<210> SEQ ID NO 37
<211> LENGTH: 22
<212> TYPE: DNA
<213> ORGANISM: Artificial sequence
<220> FEATURE:
<223> OTHER INFORMATION: colanic acid primer

<400> SEQUENCE: 37
gttatcgatg atcaggttgc gc                                                  22

<210> SEQ ID NO 38
<211> LENGTH: 45
<212> TYPE: DNA
<213> ORGANISM: Artificial sequence
<220> FEATURE:
<223> OTHER INFORMATION: colanic acid primer

<400> SEQUENCE: 38
gaagcagctc cagcctacac cgccagcttg ctgcaggctt tatag                         45

<210> SEQ ID NO 39
<211> LENGTH: 39
<212> TYPE: DNA
<213> ORGANISM: Artificial sequence
<220> FEATURE:
<223> OTHER INFORMATION: colanic acid primer

<400> SEQUENCE: 39
ctaaggagga tattcattgt ttatttatca ctttggcag                                39

<210> SEQ ID NO 40
<211> LENGTH: 23
<212> TYPE: DNA
<213> ORGANISM: Artificial sequence
<220> FEATURE:
<223> OTHER INFORMATION: colanic acid primer

<400> SEQUENCE: 40
gtaataacct cacattatcc ctg                                                 23

<210> SEQ ID NO 41
<211> LENGTH: 20
<212> TYPE: DNA
<213> ORGANISM: Artificial sequence
<220> FEATURE:
<223> OTHER INFORMATION: colanic acid primer

<400> SEQUENCE: 41
gtgtaggctg gagctgcttc                                        20

<210> SEQ ID NO 42
<211> LENGTH: 20
<212> TYPE: DNA
<213> ORGANISM: Artificial sequence
<220> FEATURE:
<223> OTHER INFORMATION: colanic acid primer

<400> SEQUENCE: 42
gtgtaggctg gagctgcttc                                        20

<210> SEQ ID NO 43
<211> LENGTH: 26
<212> TYPE: DNA
<213> ORGANISM: Artificial sequence
<220> FEATURE:
<223> OTHER INFORMATION: pgaDABC primer

<400> SEQUENCE: 43
atgtattcaa gtagcagaaa aaggtg                                 26

<210> SEQ ID NO 44
<211> LENGTH: 48
<212> TYPE: DNA
<213> ORGANISM: Artificial sequence
<220> FEATURE:
<223> OTHER INFORMATION: pgaDABC primer

<400> SEQUENCE: 44
gaagcagctc cagcctacac ggttattgct gagtgctgat tttagtgc          48

<210> SEQ ID NO 45
<211> LENGTH: 43
<212> TYPE: DNA
<213> ORGANISM: Artificial sequence
<220> FEATURE:
<223> OTHER INFORMATION: pgaDABC primer

<400> SEQUENCE: 45
ctaaggagga tattcatgtc tgggcgctgt acaataagct gcg               43

<210> SEQ ID NO 46
<211> LENGTH: 30
<212> TYPE: DNA
<213> ORGANISM: Artificial sequence
<220> FEATURE:
<223> OTHER INFORMATION: pgaDABC primer

<400> SEQUENCE: 46
ttatgcccgg actagcgctt tttctgaaac                             30

<210> SEQ ID NO 47
<211> LENGTH: 20
<212> TYPE: DNA
<213> ORGANISM: Artificial sequence
<220> FEATURE:
<223> OTHER INFORMATION: pgaDABC primer

<400> SEQUENCE: 47
gtgtaggctg gagctgcttc                                        20

```
<210> SEQ ID NO 48
<211> LENGTH: 20
<212> TYPE: DNA
<213> ORGANISM: Artificial sequence
<220> FEATURE:
<223> OTHER INFORMATION: pgaDABC primer

<400> SEQUENCE: 48
atgggaatta gccatggtcc                                               20
```